United States Patent
Desai et al.

(10) Patent No.: US 7,220,434 B2
(45) Date of Patent: May 22, 2007

(54) DUAL-RELEASE COMPOSITIONS OF A CYCLOOXYGENASE-2 INHIBITOR

(75) Inventors: Subhash Desai, Wilmette, IL (US); Sreekant R. Nadkarni, Gurnee, IL (US); Randy J. Wald, Portage, MI (US); Gary A. DeBrincat, Battle Creek, MI (US)

(73) Assignee: Pharmacia Corporation (of Pfizer, Inc.), St Louis, MO (US)

( * ) Notice: Subject to any disclaimer, the term of this patent is extended or adjusted under 35 U.S.C. 154(b) by 2 days.

(21) Appl. No.: 10/169,039

(22) PCT Filed: Dec. 20, 2000

(86) PCT No.: PCT/US00/34754

§ 371 (c)(1),
(2), (4) Date: Feb. 23, 2004

(87) PCT Pub. No.: WO01/45706

PCT Pub. Date: Jun. 28, 2001

(65) Prior Publication Data

US 2004/0242640 A1    Dec. 2, 2004

(51) Int. Cl.
*A61K 9/14* (2006.01)

(52) U.S. Cl. .................................................. 424/501
(58) Field of Classification Search ................. 424/490
See application file for complete search history.

(56) References Cited

U.S. PATENT DOCUMENTS 5,478,573 A * 12/1995 Eichel et al. ............... 424/480
5,662,883 A * 9/1997 Bagchi et al. .............. 424/9.4
5,932,598 A * 8/1999 Talley et al. ................ 514/341

FOREIGN PATENT DOCUMENTS

EP    1049467 A1 * 11/2000

* cited by examiner

Primary Examiner—Michael G. Hartley
Assistant Examiner—Nabila Ebrahim
(74) Attorney, Agent, or Firm—Patricia K. Fitzsimmons; Charles W. Ashbrook

(57) ABSTRACT

Pharmaceutical compositions are provided comprising one or more orally deliverable dose units, each comprising a selective cyclooxygenase-2 inhibitory drug of low water solubility, for example celecoxib, in an immediate-release fraction and a controlled-release, slow-release, programmed-release, timed-release, pulse-release, sustained-release or extended-release fraction. The compositions are useful in treatment or prophylaxis of cyclooxygenase-2 mediated conditions and disorders.

18 Claims, 1 Drawing Sheet

DUAL-RELEASE COMPOSITIONS OF A CYCLOOXYGENASE-2 INHIBITOR

FIELD OF THE INVENTION

The present invention relates to orally deliverable pharmaceutical compositions containing a selective cyclooxygenase-2 (COX-2) inhibitory drug as an active ingredient, to processes for preparing such compositions, to methods of treatment of COX-2 mediated disorders comprising orally administering such compositions to a subject, and to use of such compositions in the manufacture of medicaments.

BACKGROUND OF THE INVENTION

Numerous compounds have been reported having therapeutically and/or prophylactically useful selective COX-2 inhibitory effect, and having utility in treatment or prevention of specific COX-2 mediated disorders or of such disorders in general. Among such compounds are a large number of substituted pyrazolyl benzenesulfonamides as reported in U.S. Pat. No. 5,760,068 to Talley et al., including for example the compound 4-[5-(4-methylphenyl)-3-(trifluoromethyl)-1H-pyrazol-1-yl]benzenesulfonamide, also referred to herein as celecoxib (I), and the compound 4-[5-(3-fluoro-4-methoxyphenyl)-3-difluoromethyl)-1H-pyrazol-1-yl]benzenesulfonamide, also referred to herein as deracoxib (II).

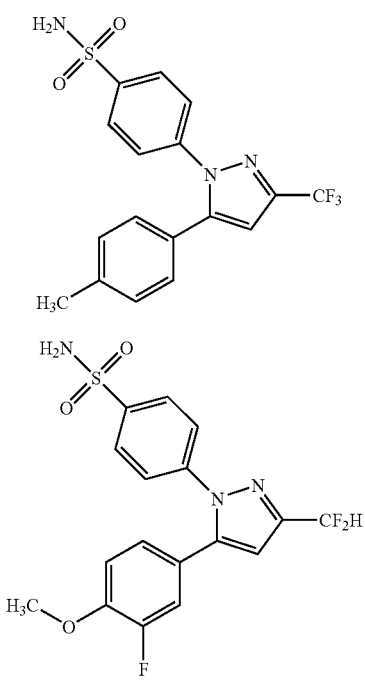

Other compounds reported to have therapeutically and/or prophylactically useful selective COX-2 inhibitory effect are substituted isoxazolyl benzenesulfonamides as reported in U.S. Pat. No. 5,633,272 to Talley et al., including the compound 4-[5-methyl-3-phenylisoxazol-4-yl]benzenesulfonamide, also referred to herein as valdecoxib (III).

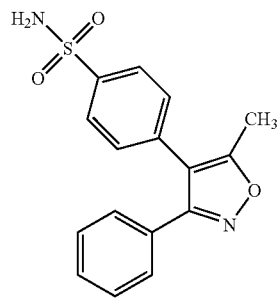

Still other compounds reported to have therapeutically and/or prophylactically useful selective COX-2 inhibitory effect are substituted (methylsulfonyl)phenyl furanones as reported in U.S. Pat. No. 5,474,995 to Ducharme et al., including the 5 compound 3-phenyl-4-[4-(methylsulfonyl)phenyl]-5H-furan-2-one, also referred to herein as rofecoxib (IV).

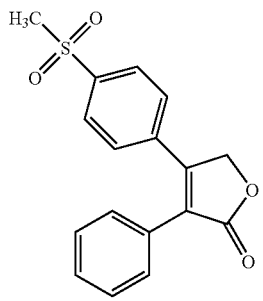

U.S. Pat. No. 5,981,576 to Belley et al. discloses a further series of (methylsulfonyl)phenyl furanones said to be useful as selective COX-2 inhibitory drugs, including 3-(1-cyclopropylmethoxy)-5,5-dimethyl-4-[4-(methylsulfonyl)phenyl]-5H-furan-2-one and 3-(1-cyclopropylethoxy)-5,5-dimethyl-4-[4-(methylsulfonyl)phenyl]-5H-furan-2-one.

U.S. Pat. No. 5,861,419 to Dube et al. discloses substituted pyridines said to be useful as selective COX-2 inhibitory drugs, including for example the compound 5-chloro-3-(4-methylsulfonyl)phenyl-2-(2-methyl-5-pyridinyl)pyridine (V).

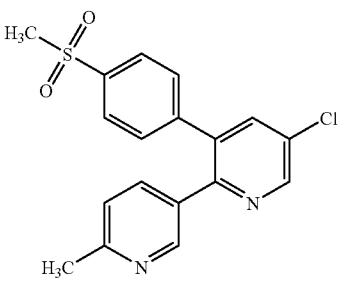

European Patent Application No. 0 863 134 discloses the compound 2-(3,5-difluorophenyl)-3-[4-(methylsulfonyl)phenyl]-2-cyclopenten-1-one said to be useful as a selective COX-2 inhibitory drug.

U.S. Pat. No. 6,034,256 discloses a series of benzopyrans said to be useful as selective COX-2 inhibitory drugs, including the compound (S)-6,8-dichloro-2-(trifluoromethyl)-2H-1-benzopyran-3-carboxylic acid (VI).

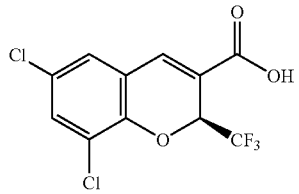

(VI)

Many selective COX-2 inhibitory drugs, including celecoxib, deracoxib, valdecoxib and rofecoxib, are hydrophobic and have low solubility in water. This has presented practical difficulties in formulating such drugs for oral administration, particularly where early onset of therapeutic effect is desired or required.

Illustratively, the formulation of celecoxib for effective oral administration to a subject has hitherto been complicated by the unique physical and chemical properties of celecoxib, particularly its low solubility and factors associated with its crystal structure, including cohesiveness, low bulk density and low compressibility. Celecoxib is unusually insoluble in aqueous media. Unformulated celecoxib is not readily dissolved and dispersed for rapid absorption in the gastrointestinal tract when administered orally, for example in capsule form. In addition, unformulated celecoxib, which has a crystal morphology that tends to form long cohesive needles, typically fuses into a monolithic mass upon compression in a tableting die. Even when blended with other substances, the celecoxib crystals tend to separate from the other substances and agglomerate together during mixing of the composition resulting in a non-uniformly blended composition containing undesirably large aggregates of celecoxib. Therefore, it is difficult to prepare a pharmaceutical composition containing celecoxib that has the desired blend uniformity. Further, handling problems arising for example from the low bulk density of celecoxib are encountered during preparation of celecoxib compositions. Accordingly, a need exists for solutions to numerous problems associated with preparation of compositions and dosage forms comprising celecoxib, particularly orally deliverable dose units.

In general, a need exists for orally deliverable formulations of a selective COX-2 inhibitor drug of low water solubility, such formulations possessing one or more of the following characteristics relative to the unformulated drug or to other compositions of the drug:

(1) improved solubility;
(2) shorter disintegration time;
(3) shorter dissolution time;
(4) decreased tablet friability;
(5) increased tablet hardness;
(6) improved wettability;
(7) improved compressibility;
(8) improved flow properties of liquid and particulate solid compositions;
(9) improved physical stability of the finished composition;
(10) reduced tablet or capsule size;
(11) improved blend uniformity;
(12) improved dose uniformity;
(13) improved control of weight variation during encapsulation and/or tableting;
(14) increased granule density for wet granulated compositions;
(15) reduced water requirement for wet granulation;
(16) reduced wet granulation time; and
(17) reduced drying time for wet granulated mixtures.

More specifically, there exists an especial need for orally deliverable formulations of a selective COX-2 inhibitory drug of low water solubility such as celecoxib, such formulations providing both rapid onset of therapeutic effect and longer duration of therapeutic effect than the unformulated drug or known formulations of the drug. To the extent that rapid onset of therapeutic effect is related to pharmacokinetic parameters such as a high maximum blood serum concentration of the drug ($C_{max}$) and a short time from oral administration to reach such maximum blood serum concentration ($T_{max}$), there is an especial need for orally deliverable formulations of the drug providing a greater $C_{max}$ and/or an earlier $T^{max}$ than the unformulated drug or known formulations of the drug. At the same time, to the extent that long duration of therapeutic effect is related to pharmacokinetic parameters such as long half-life of blood serum concentration of the drug after $C_{max}$ is reached, also known as terminal half-life ($T_{1/2}$), there is an especial need for orally deliverable formulations of the drug providing a longer $T_{1/2}$ than the unformulated drug or known formulations of the drug. A single composition that satisfies both the need for a greater $C_{max}$ and/or an earlier $T_{max}$ and the need for a greater $T_{1/2}$ would dramatically enhance the therapeutic utility of selective COX-2 inhibitory drugs in a wide variety of situations.

As is indicated hereinbelow, treatment with selective COX-2 inhibitory drugs is indicated or potentially indicated in a very wide array of COX-2 mediated conditions and disorders. It would be of benefit to provide formulations exhibiting pharmacokinetics consistent with rapid onset and long duration of therapeutic effect especially for treatment of disorders where early relief from pain or other symptoms is desired or required and where once-a-day administration is required or preferred.

Selective COX-2 inhibitory drugs including celecoxib that are of low solubility in water are conveniently formulated in solid particulate form. The individual or primary particles of the drug can dispersed in a liquid medium, as in a suspension formulation, or can be aggregated to form secondary particles or granules that can be encapsulated to provide a capsule dosage form, or compressed or molded to provide a tablet dosage form.

Numerous processes are known and used in the art for preparing drug formulations having primary particle sizes in a desired range, or having a desired mean particle size, or having a particle size distribution characterized by a parameter such as $D_{90}$, which is defined herein as a linear measure of diameter having a value such that 90% by volume of particles in the formulation, in the longest dimension of the particles, are smaller than that diameter. For practical purposes a determination of $D_{90}$ based on 90% by weight rather than by volume is generally suitable.

For consistency with prior publications, the terms "microparticle" and "nanoparticle" are defined herein as in U.S. Pat. No. 5,384,124 to Courteille et al., to refer to particles having respectively a diameter of between 1 µm and 2000 µm, and a diameter of less than 1 µm (1000 nm). The preparation of microparticles and nanoparticles, according to U.S. Pat. No. 5,384,124, "is principally used to retard dissolution of active principles". However, U.S. Pat. No.

5,145,684 to Liversidge et al. discloses nanoparticulate compositions said to provide "unexpectedly high bioavailability" of drugs, particularly drugs having low solubility in a liquid medium such as water. International Publication No. WO 93/25190 provides pharmacokinetic data from a rat study indicating a higher apparent rate of absorption from oral administration of a nanoparticulate (average particle size 240–300 nm) than from oral administration of a microparticulate (particle size range 20–30 μm) dispersion of naproxen.

Illustrative processes that have been contemplated for preparing poorly water soluble drugs in nanoparticulate form are disclosed in the patents and publications listed below, each of which is individually incorporated herein by reference.

U.S. Pat. No. 4,826,689 to Violanto & Fischer.
Above-cited U.S. Pat. No. 5,145,684.
U.S. Pat. No. 5,298,262 to Na & Rajagopalan.
U.S. Pat. No. 5,302,401 to Liversidge et al.
U.S. Pat. No. 5,336,507 to Na & Rajagopalan.
U.S. Pat. No. 5,340,564 to Illig & Sarpotdar.
U.S. Pat. No. 5,346,702 to Na & Rajagopalan.
U.S. Pat. No. 5,352,459 to Hollister et al.
U.S. Pat. No. 5,354,560 to Lovrecich.
Above-cited U.S. Pat. No. 5,384,124.
U.S. Pat. No. 5,429,824 to June.
U.S. Pat. No. 5,503,723 to Ruddy et al.
U.S. Pat. No. 5,510,118 to Bosch et al.
U.S. Pat. No. 5,518,187 to Bruno et al.
U.S. Pat. No. 5,518,738 to Eickhoff et al.
U.S. Pat. No. 5,534,270 to De Castro.
U.S. Pat. No. 5,536,508 to Canal et al.
U.S. Pat. No. 5,552,160 to Liversidge et al.
U.S. Pat. No. 5,560,931 to Eickhoff et al.
U.S. Pat. No. 5,560,932 to Bagchi et al.
U.S. Pat. No. 5,565,188 to Wong et al.
U.S. Pat. No. 5,569,448 to Wong et al.
U.S. Pat. No. 5,571,536 to Eickhoff et al.
U.S. Pat. No. 5,573,783 to Desieno & Stetsko.
U.S. Pat. No. 5,580,579 to Ruddy et al.
U.S. Pat. No. 5,585,108 to Ruddy et al.
U.S. Pat. No. 5,587,143 to Wong.
U.S. Pat. No. 5,591,456 to Franson et al.
U.S. Pat. No. 5,622,938 to Wong.
U.S. Pat. No. 5,662,883 to Bagchi et al.
U.S. Pat. No. 5,665,331 to Bagchi et al.
U.S. Pat. No. 5,718,919 to Ruddy et al.
U.S. Pat. No. 5,747,001 to Wiedmann et al.
Above-cited International Patent Publication No. WO 93/25190.
International Patent Publication No. WO 96/24336.
International Patent Publication No. WO 97/14407.
International Patent Publication No. WO 98/35666.
International Patent Publication No. WO 99/65469.
International Patent Publication No. WO 00/18374.
International Patent Publication No. WO 00/27369.
International Patent Publication No. WO 00/30615.

Alternatively, drugs of low water solubility have sometimes been formulated in solution in a pharmaceutically acceptable solvent such as polyethylene glycol. Solution formulations typically permit rapid absorption of the dissolved drug, in some cases giving even more rapid onset of therapeutic effect than is possible with nanoparticulate formulations.

Solutions and suspensions of nanoparticles and/or microparticles can be formulated as liquid dosage forms, the required dose being measured, for example using a cup, at the time of administration. Alternatively, solutions and suspensions can be formulated as flowable liquids or as gels in unit dose articles such as sachets or soft capsules. Sachets are opened and only the contents administered orally to the subject; soft capsules are a more convenient dosage form as the entire capsule is orally administered. Typically soft capsule walls are composed predominantly of gelatin and the terms "softgel" or "gelcap" are sometimes used to describe these formulations.

Anti-inflammatory, antipyretic and analgesic drugs, for example nonsteroidal anti-inflammatory drugs (NSAIDs) and opioids have not frequently been formulated as rapid-release solutions, gels or soft capsules for oral administration. However, illustrative processes for preparing such formulations are disclosed in the patents and publications listed below, each of which is individually incorporated herein by reference.

U.S. Pat. No. 5,859,060 to Platt.
European Patent Application No. 0 945 131.
Japanese Laid-Open Patent Application No. 03/106815.

Extending the half-life of an orally administered drug is achievable by a variety of controlled-release, slow-release, programmed-release, timed-release, pulse-release, sustained-release or extended-release technologies known in the art. Typically such technologies involve formulating the drug in a polymer matrix from which the drug is gradually released, or protecting the drug from immediate release by means of a barrier layer which degrades over time in the gastrointestinal tract. Examples of barrier layers include liposomes, nanocapsules, microcapsules and coatings on granules, beads or tablets. Dosage forms can be liquids (e.g., suspensions) or unit dose articles (e.g., tablets, capsules, soft capsules).

Illustrative processes that have been contemplated for preparing controlled-release, slow-release, programmed-release, timed-release, pulse-release, sustained-release or extended-release formulations of opioids, NSAIDs and other analgesic, antipyretic and anti-inflammatory drugs are disclosed in the patents and publications listed below, each of which is individually incorporated herein by reference.

U.S. Pat. No. 3,362,880 to Jeffries.
U.S. Pat. No. 4,308,251 to Dunn & Lampard.
U.S. Pat. No. 4,316,884 to Alam & Eichel.
U.S. Pat. No. 4,571,333 to Hsias & Kent.
U.S. Pat. No. 4,601,894 to Hanna & Vadino.
U.S. Pat. No. 4,708,861 to Popescu et al.
U.S. Pat. No. 4,749,575 to Rotman.
U.S. Pat. No. 4,765,989 to Wong et al.
U.S. Pat. No. 4,795,641 to Kashdan.
U.S. Pat. No. 4,803,079 to Hsias & Kent.
U.S. Pat. No. 4,847,093 to Ayer & Wong.
U.S. Pat. No. 4,867,985 to Heafield et al.
U.S. Pat. No. 4,892,778 to Theeuwes et al.
U.S. Pat. No. 4,940,588 to Sparks & Geoghegan.
U.S. Pat. No. 4,975,284 to Stead & Nabahi.
U.S. Pat. No. 4,980,175 to Chavkin & Mackles.
U.S. Pat. No. 5,055,306 to Barry et al.
U.S. Pat. No. 5,082,668 to Wong et al.
U.S. Pat. No. 5,160,742 to Mazer et al.
U.S. Pat. No. 5,160,744 to Jao et al.
U.S. Pat. No. 5,190,765 to Jao et al.
U.S. Pat. No. 5,273,760 to Oshlack et al.
U.S. Pat. No. 5,275,820 to Chang.
U.S. Pat. No. 5,292,534 to Valentine & Valentine.
U.S. Pat. No. 5,296,236 to Santus & Golzi.
U.S. Pat. No. 5,415,871 to Pankhania et al.
U.S. Pat. No. 5,427,799 to Valentine & Valentine.

U.S. Pat. No. 5,451,409 to Rencher et al.
U.S. Pat. No. 5,455,046 to Baichwal.
U.S. Pat. No. 5,460,825 to Roche.
U.S. Pat. No. 5,472,711 to Baichwal.
U.S. Pat. No. 5,472,712 to Oshlack et al.
U.S. Pat. No. 5,478,574 to Mendell.
U.S. Pat. No. 5,518,730 to Fuisz.
U.S. Pat. No. 5,523,095 to Modi.
U.S. Pat. No. 5,527,545 to Santus et al.
U.S. Pat. No. 5,536,505 to Wilson et al.
U.S. Pat. No. 5,571,533 to Santus et al.
U.S. Pat. No. 5,674,533 to Santus et al.
U.S. Pat. No. 5,773,025 to Baichwal.
U.S. Pat. No. 5,858,344 to Müller & Cremer.
U.S. Pat. No. 6,093,420 to Baichwal.
International Patent Publication No. WO 87/00044.
International Patent Publication No. WO 89/08119.
International Patent Publication No. WO 91/16920.
International Patent Publication No. WO 92/13547.
International Patent Publication No. WO 93/10760.
International Patent Publication No. WO 93/10769.
International Patent Publication No. WO 93/12765.
International Patent Publication No. WO 93/17673.
International Patent Publication No. WO 95/14460.
International Patent Publication No. WO 96/16638.
International Patent Publication No. WO 98/01117.
International Patent Publication No. WO 99/12524.
International Patent Publication No. WO 99/51209.
International Patent Publication No. WO 99/61005.
Belgian Patent Application No. 900 824.
European Patent Application No. 0 147 780.
European Patent Application No. 0 438 249.
European Patent Application No. 0 516 141.
European Patent Application No. 0 875 245.
European Patent Application No. 0 945 137.
French Patent Application No. 2 584 604.
Japanese Laid-Open Patent Application No. 56/030402.
Japanese Laid-Open Patent Application No. 60/072,813.
Japanese Laid-Open Patent Application No. 63/174925.
Japanese Laid-Open patent application Ser. No. 10/298,064.

Attempts have been made to formulate certain NSAIDs, opioids or other analgesic, antipyretic or anti-inflammatory drugs in single dual-release compositions having both an immediate-release fraction and a controlled-release, slow-release, programmed-release, timed-release, pulse-release, sustained-release or extended-release fraction of the drug. Such compositions have been disclosed, for example, for NSAIDs generally in the patents and publications listed below, each of which is individually incorporated herein by reference.

U.S. Pat. No. 4,980,170 to Schneider et al.
International Publication No. WO 99/12524.

Such dual-release compositions have illustratively been disclosed for ibuprofen in the patents and publications listed below, each of which is individually incorporated herein by reference.

U.S. Pat. No. 5,681,583 to Conte et al.
International Publication No. WO 96/41617.

Such dual-release compositions have illustratively been disclosed for naproxen in the patents listed below, each of which is individually incorporated herein by reference.

U.S. Pat. No. 4,888,178 to Rotini & Marchi.
U.S. Pat. No. 5,609,884 to Desai.

Several factors influence dissolution in a solvent medium of a drug from its carrier, including the surface area of the drug presented to the solvent medium, the solubility of the drug in the solvent medium, and the driving forces of the saturation concentration of dissolved materials in the solvent medium. Notwithstanding these factors, a strong correlation has been established between the in vitro dissolution time determined for a dosage form and the in vivo drug release rate. This correlation is so firmly established in the art that dissolution time has become generally descriptive of drug release potential for the active component of the particular unit dosage composition. In view of this relationship, it is clear that dissolution time determined for a composition is one of the important fundamental characteristics for consideration when evaluating dual-release compositions.

Selective COX-2 inhibitory drugs have not previously been formulated in dual-release dosage forms. Certain drugs of this class have a sufficiently long half-life, even when conventionally formulated for oral delivery, to be suitable for once-a-day administration. For example, Canadian Patent Application No. 2,254,061 discloses that rofecoxib has a half-life sufficient to provide therapeutic benefit over a 24-hour period.

SUMMARY OF THE INVENTION

According to the present invention, a selective COX-2 inhibitory drug of low water solubility is formulated in an orally deliverable dosage form having dual-release properties such that onset of therapeutic effect is more rapid, yet at the same time the duration of therapeutic effect is longer, than is achieved with known formulations of the drug.

It is contemplated that such a drug, for example celecoxib, provides more rapid onset of therapeutic effect if, upon oral administration of a composition comprising the drug, the drug exhibits pharmacokinetic properties leading to a greater maximum blood serum concentration ($C_{max}$) and/or a shorter time following the administration to reach that maximum ($T_{max}$) or to reach a threshold concentration for therapeutic effect.

In the case of celecoxib, the threshold blood serum concentration consistent with therapeutic effect depends on the individual subject, the nature of the disorder being treated and other factors, but for present purposes is about 50 ng/ml. For selective COX-2 inhibitory drugs generally, the threshold concentration is that providing therapeutic effect equivalent to celecoxib at a blood serum concentration of about 50 ng/ml.

An embodiment of the invention is a composition comprising a selective COX-2 inhibitory drug of low water solubility, preferably celecoxib, that, upon oral administration thereof to a subject, exhibits pharmacokinetic properties leading to (a) a greater maximum blood serum celecoxib concentration ($C_{max}$) and/or a shorter time following the administration to reach a threshold concentration for therapeutic effect, and (b) a longer terminal half-life of blood serum drug concentration ($T_{1/2}$), than previous compositions.

It is contemplated that a greater $C_{max}$ and/or a shorter time to reach the threshold concentration (i.e., immediate release properties) are obtained by providing a first fraction of the drug in the composition (i) in the form of solid particles having a $D_{50}$ particle size less than about 5 µm, or (ii) in solution in a pharmaceutically acceptable solvent. Preferably the composition also exhibits a shorter $T_{max}$ than previous compositions.

It is contemplated that a longer $T_{1/2}$ is obtained by providing a second fraction of the drug in the composition (i) in the form of solid particles having a $D_{90}$ particle size greater than about 25 µm, or (ii) in the form of particles of any convenient $D_{90}$ particle size providing controlled release, slow release, programmed release, timed release, pulse release, sustained release or extended release of celecoxib. Preferably the $T_{1/2}$ thereby obtained results in maintenance of a therapeutically effective blood serum concentration of drug for at least about 24 hours following oral administration.

Accordingly, there is now provided a pharmaceutical composition comprising one or more orally deliverable dose units, each comprising a first fraction of a selective COX-2 inhibitory drug of low water solubility, illustratively celecoxib in an amount of about 10 mg to about 400 mg, this first fraction being in solution in a pharmaceutically acceptable solvent and/or present in immediate-release solid particles having a $D_{50}$ particle size less than about 5 μm and preferably a $D_{90}$ particle size less than about 5 μm; and a second fraction of the drug, illustratively celecoxib in an amount of about 10 mg to about 400 mg, this second fraction being present in solid particles having a $D_{90}$ particle size greater than about 25 μm and/or in controlled-release, slow-release, programmed-release, timed-release, pulse-release, sustained-release or extended-release particles; wherein the first fraction and the second fraction of the drug are present in a weight ratio of about 10:1 to about 1:10. Where the drug is other than celecoxib, the amount of the drug in each of the first and second fractions is an amount that is therapeutically equivalent to about 10 mg to about 400 mg of celecoxib.

In one embodiment, the immediate-release particles have a $D_{90}$ particle size less than about 1 μm. In another embodiment, the immediate-release particles have a $D_{50}$ particle size of about 0.45 to about 5 μm.

The dose units comprising the composition can be in the form of discrete solid articles such as tablets, pills, hard or soft capsules, lozenges, sachets or pastilles; alternatively the composition can be in the form of a substantially homogeneous flowable mass, such as a particulate or granular solid or a liquid suspension, from which single dose units are measurably removable.

In a particularly preferred embodiment the dose units are tablets each comprising a first fraction of a selective COX-2 inhibitory drug of low water solubility, illustratively celecoxib in an amount of about 10 mg to about 400 mg, this first fraction being present in immediate-release solid particles having a $D_{50}$ particle size less than about 5 μm; and a second fraction of the drug, illustratively celecoxib in an amount of about 10 mg to about 400 mg, this second fraction being distributed in a sustained-release matrix comprising hydroxypropylmethylcellulose (HPMC) having a viscosity, 2% in water, of about 100 to about 8000 cP; wherein the first fraction and the second fraction are present in a weight ratio of about 10:1 to about 1:10. The two fractions of the drug can be more or less homogeneously distributed throughout each tablet, but preferably the two fractions are individually contained in discrete layers or zones of each tablet. Again, where the drug is other than celecoxib, the amount of the drug in each of the first and second fractions is an amount that is therapeutically equivalent to about 10 mg to about 400 mg of celecoxib.

In another particularly preferred embodiment the dose units are tablets or, more preferably, capsules each comprising a first fraction of a selective COX-2 inhibitory drug of low water solubility, illustratively celecoxib in an amount of about 10 mg to about 400 mg, this first fraction being present in immediate-release solid particles having a $D_{50}$ particle size less than about 5 μm; and a second fraction of the drug, illustratively in an amount of about 10 mg to about 400 mg, this second fraction being present in a multiplicity of solid beads each having a sustained-release coating that comprises one or more pharmaceutically acceptable swellable or erodible polymers; wherein the first fraction and the second fraction are present in a weight ratio of about 10:1 to about 1:10. A swellable polymer is a polymer that, when placed in an aqueous medium, absorbs water and swells. An erodible polymer is defined herein as a polymer that, when placed in an aqueous medium, progressively from the outside of the tablet or bead inward to the center thereof, dissolves or disperses in the medium.

In a related embodiment, the polymer is neither highly swellable nor erodible as defined above, but, when present as a coating on a tablet or bead comprising a drug, has release-extending properties. Such a polymer is preferably used in combination with a water-soluble polymer such that when the coated tablet or bead is placed in an aqueous medium the coating becomes porous and permits slow release of the drug.

Preferred polymers are ethylcellulose and polymers and copolymers of acrylic acid, methacrylic acid and esters thereof. Preferably the first fraction of the drug is present in a multiplicity of solid beads similar in size to the beads containing the second fraction but having no coating or having a coating that is not a sustained-release coating. Again, where the drug is other than celecoxib, the amount of the drug in each of the first and second fractions is an amount that is therapeutically equivalent to about 10 mg to about 400 mg of celecoxib.

Also provided is a method of treating a medical condition or disorder in a subject where treatment with a COX-2 inhibitor is indicated, comprising orally administering one or more dose units, typically 1 to about 4 dose units, of a composition of the invention once a day.

Also provided is a method of use of a composition of the invention in manufacture of a medicament useful in treatment and/or prophylaxis of a COX-2 mediated condition or disorder, in particular such a conditions or disorder where a combination of rapid onset and long duration of therapeutic effect is desired or required.

Other features of this invention will be in part apparent and in part pointed out hereinafter.

DETAILED DESCRIPTION OF THE INVENTION

Figure 1:
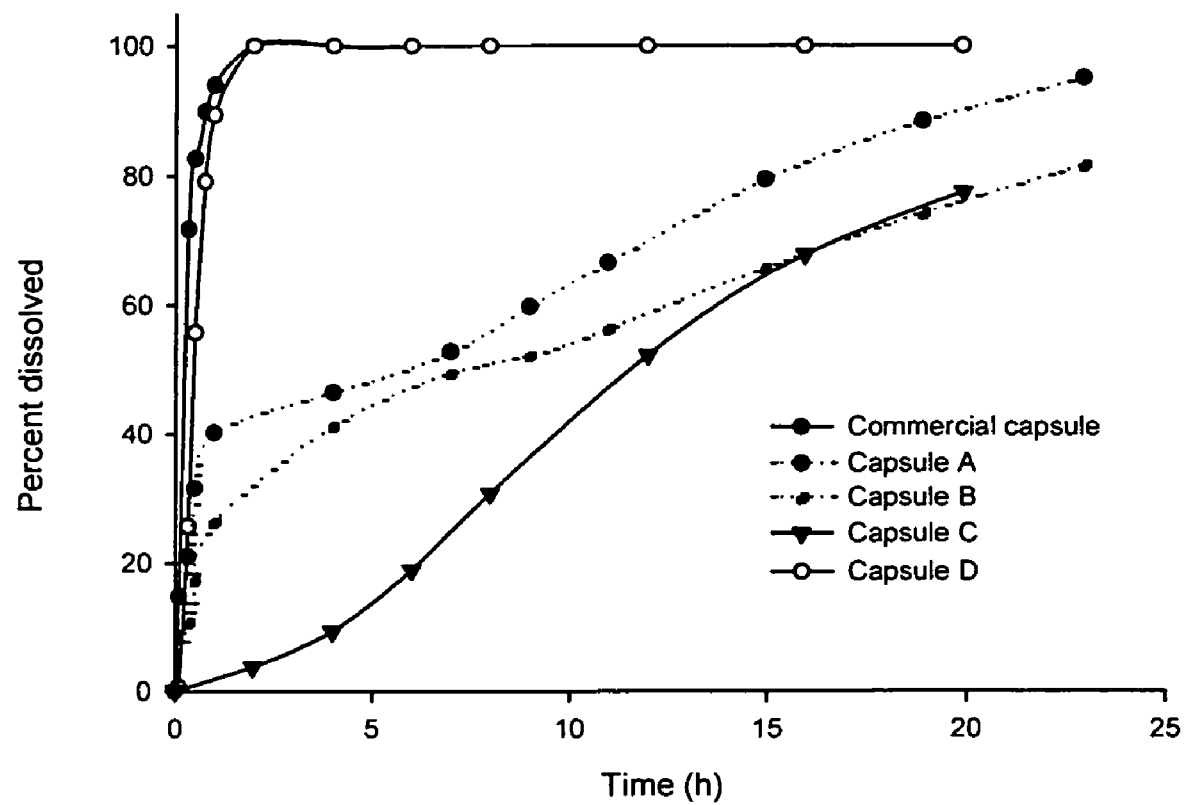
FIG. 1 shows in vitro dissolution profiles of four celecoxib capsule formulations A–D by comparison with a commercial celecoxib capsule.

The term "oral administration" herein includes any form of delivery of a therapeutic agent or a composition thereof to a subject wherein the agent or composition is placed in the mouth of the subject, whether or not the agent or composition is swallowed. Thus "oral administration" includes buccal and sublingual as well as esophageal administration. Absorption of the agent can occur in any part or parts of the gastrointestinal tract including the mouth, esophagus, stomach, duodenum, ileum and colon.

The term "orally deliverable" herein means suitable for oral administration.

A "subject" herein to which a therapeutic agent or composition thereof can be administered includes a human patient of either sex and of any age, and also includes any nonhuman animal, particularly a domestic or companion animal, illustratively a cat, dog or horse.

The term "dose unit" herein means a portion of a pharmaceutical composition that contains an amount of a therapeutic agent, in the present case a selective COX-2 inhibitory drug, suitable for a single oral administration to provide a therapeutic effect. Typically one dose unit, or a small plurality (up to about 4) of dose units, provides a sufficient amount of the agent to result in the desired effect.

The term "present in solid particles" as applied to a drug herein encompasses compositions wherein the solid particles consist essentially of the drug and compositions wherein the solid particles comprise the drug in intimate mixture with one or more other ingredients. These other ingredients can include one or more therapeutic agents other than the drug and/or one or more pharmaceutically acceptable excipients.

The terms "controlled-release", "slow-release", "programmed-release", "timed-release", "pulse-release", "sustained-release" and "extended-release" in relation to particles or formulations herein have meanings as accorded in the above-cited references. Suitable processes for preparing such "controlled-release", "slow-release", "programmed-release", "timed-release", "pulse-release", "sustained-release" or "extended-release" particles comprising celecoxib useful in compositions of the present invention include those disclosed for other drugs in the above-cited references.

The term "excipient" herein means any substance, not itself a therapeutic agent, used as a carrier or vehicle for delivery of a therapeutic agent to a subject or added to a pharmaceutical composition to improve its handling, storage, disintegration, dispersion, dissolution, release or organoleptic properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition.

The term "substantially homogeneous" with reference to a pharmaceutical composition that comprises several components means that the components are sufficiently mixed such that individual components are not present as discrete layers and do not form concentration gradients within the composition.

Novel pharmaceutical compositions according to the present invention comprise one or more orally deliverable dose units. Each dose unit comprises a selective COX-2 inhibitory drug of low water solubility, illustratively celecoxib in a therapeutically effective total amount of about 20 mg to about 800 mg, partitioned between two fractions each of about 10 mg to about 400 mg as described herein. Where the drug is other than celecoxib, the amount of the drug in each of the first and second fractions is an amount that is therapeutically equivalent to about 10 mg to about 400 mg of celecoxib.

Compositions of the invention comprise one or more orally deliverable dose units. Each dose unit comprises the drug in a therapeutically effective amount that is preferably about 5 mg to about 1000 mg, more preferably about 10 mg to about 1000 mg.

It will be understood that a therapeutically effective amount of a selective COX-2 inhibitory drug for a subject is dependent inter alia on the body weight of the subject. Where the drug is celecoxib and the subject is a child or a small animal (e.g., a dog), for example, an amount of celecoxib relatively low in the preferred range of about 10 mg to about 1000 mg is likely to provide blood serum concentrations consistent with therapeutic effectiveness. Where the subject is an adult human or a large animal (e.g., a horse), achievement of such blood serum concentrations of celecoxib are likely to require dose units containing a relatively greater amount of celecoxib. For an adult human, a therapeutically effective amount of celecoxib per dose unit in a composition of the present invention is typically about 50 mg to about 400 mg. Especially preferred amounts of celecoxib per dose unit are about 100 mg to about 200 mg, for example about 100 mg or about 200 mg.

For other selective COX-2 inhibitory drugs, an amount of the drug per dose unit can be in a range known to be therapeutically effective for such drugs. Preferably, the amount per dose unit is in a range providing therapeutic equivalence to celecoxib in the dose ranges indicated immediately above.

In one embodiment, the first fraction of the drug in a composition of the invention, which is the fraction providing immediate release, is in the form of particles having a $D_{50}$ particle size less than about 5 μm, and preferably having a $D_{90}$ particle size less than about 5 μm.

In another embodiment, the immediate-release particles have a $D_{90}$ particle size less than about 1 μm. Typically in this embodiment substantially all the particles are nanoparticles, i.e., solid particles of diameter less than 1 μm in the longest dimension of the particles. In such particles, the drug can be present alone or in intimate mixture with one or more excipients.

The effects on pharmacokinetic properties of reducing particle size from the microparticle range (greater than 1 μm diameter) to the nanoparticle range is generally unpredictable for any particular drug or class of drugs. According to the present invention, a selective COX-2 inhibitory drug of low water solubility, illustratively celecoxib, in nanoparticulate form exhibits higher $C_{max}$, shorter $T_{max}$ and/or shorter time to threshold concentration than the same drug in microparticulate form having a $D_{90}$ particle size greater than about 5 μm.

Considering only the nanoparticulate component of a composition of this embodiment of the invention, average particle size is preferably about 100 nm to about 900 nm, for example about 200 nm to about 400 nm, or about 500 nm to about 900 nm. The drug can be in crystalline or amorphous form in the nanoparticles. Processes for preparing nanoparticles that involve milling or grinding typically provide the drug in crystalline form, whereas processes that involve precipitation from solution typically provide the drug in amorphous form.

In one embodiment, nanoparticles of the drug have a surface modifying agent adsorbed on the surface thereof. In another embodiment, nanoparticles of the drug are contained in a matrix formed by a polymer. Preferably excipients are present and most preferably include a water soluble diluent or wetting agent. Such a water soluble diluent or wetting agent is believed to assist in dispersion and dissolution of the drug when the composition is ingested. Preferably both a water soluble diluent and a wetting agent are present.

Nanoparticles comprising or consisting essentially of a selective COX-2 inhibitory drug of low water solubility can be prepared according to any process previously applied to preparation of other poorly water soluble drugs in nanoparticulate form. Suitable processes, without restriction, are illustratively disclosed for such other drugs in the above-cited references.

In another embodiment, the first fraction of the selective COX-2 inhibitory drug in a composition of the invention, which is the fraction providing immediate release, is in solution in a pharmaceutically acceptable solvent. Polyethylene glycol, for example polyethylene glycol having an average molecular weight of about 400 (PEG-400), has been found to be a suitable solvent, either alone or in mixture with water. Illustratively, a mixture of 2 parts PEG-400 to 1 part water has been found to be a useful solvent base for an orally deliverable celecoxib solution. According to the present invention, an orally administered selective COX-2 inhibitory drug in dissolved form exhibits higher $C_{max}$, shorter $T_{max}$ and/or shorter time to threshold concentration than the same drug in other orally administered forms so far evaluated.

Although a selective COX-2 inhibitory drug solution can be presented to a subject in bulk liquid form, it can alternatively be presented in pre-measured unit dose form, for example as a soft capsule. Optionally a pharmaceutically acceptable gelling agent can be added to the solution to form a gel. Softgels or gelcaps, which are soft capsules containing a gel, are therefore suitable dosage forms for compositions of the invention.

When administered orally to a fasting adult human, a 100 mg dose unit of a composition of the invention preferably exhibits a $T_{max}$ of less than about 1.5 h, more preferably less than about 1 h and most preferably less than about 0.75 h, and a $C_{max}$ of at least about 100 ng/ml, more preferably at least about 200 ng/ml. Typically a celecoxib composition of the invention provides a blood serum concentration of celecoxib of at least about 50 ng/ml within 30 minutes of oral administration; preferred compositions achieve such a concentration in as little as 15 minutes. This early rise in blood serum concentration is believed to be associated with the rapid onset of therapeutic effect achieved by compositions of the present invention.

In addition to the first fraction of the selective COX-2 inhibitory drug, which as explained above is the immediate-release fraction, a composition of the invention further comprises a second fraction of the drug that is the controlled-release, slow-release, programmed-release, timed-release, pulse-release, sustained-release or extended-release fraction. In one embodiment, this fraction comprises selective COX-2 inhibitory drug microparticles having a $D_{90}$ particle size greater than about 25 µm. Preferably the $D_{90}$ particle size of this fraction is about 25 µm to about 200 µm, more preferably about 25 µm to about 100 µm, for example about 40 µm to about 75 µm.

Primary particles, generated for example by milling or grinding, or by precipitation from solution, can agglomerate to form secondary aggregate particles. The term "particle size" as used herein refers to size, in the longest dimension, of primary particles, unless the context demands otherwise.

Preferably excipients are associated with or present in the primary microparticles and these excipients more preferably include a water soluble diluent or wetting agent or both.

In another embodiment, the second fraction of the selective COX-2 inhibitory drug is in the form of particles of any convenient size that are controlled-release, slow-release, programmed-release, timed-release, pulse-release, sustained-release or extended-release particles prepared by any process disclosed for drugs in the above-cited references, such process being adapted as necessary for the specific properties of the particular drug.

The particles comprising the second fraction of the selective COX-2 inhibitory drug can optionally be dispersed as a suspension in a liquid diluent. In one embodiment of the invention, the particles comprising the second fraction are in stable suspension in a matrix solution comprising the first fraction of the drug. This suspension can be presented as a bulk liquid or can be in a pre-measured dosage form such as soft capsules, optionally as softgels or gelcaps as described above.

When administered orally to a fasting adult human, a 100 mg dose unit of a composition of the invention preferably exhibits a $T_{1/2}$ of at least about 9 h, more preferably at least about 12 h and most preferably at least about 15 h. The $T_{1/2}$ is preferably such as to maintain a blood serum concentration of the selective COX-2 inhibitory drug above the threshold for therapeutic effect for about 18 h, more preferably for about 24 h, following administration. For example, where the drug is celecoxib, the $T_{1/2}$ is preferably such as to maintain a blood serum concentration of at least about 50 ng/ml, more preferably at least about 100 ng/ml, for about 18 h, more preferably for about 24 h, following administration. This maintenance of blood serum concentration is believed to be associated with the long duration of therapeutic effect achieved by oral administration of a single dose of a composition of the present invention. In particular, it is believed that this maintenance of blood serum concentration is what enables a once-a-day administration regimen for preferred compositions of the invention.

One embodiment of the invention is a pharmaceutical composition comprising one or more orally deliverable dose units, each comprising a first fraction of a selective COX-2 inhibitory drug, preferably celecoxib, in immediate-release form in an amount of about 10 mg to about 400 mg, and a second fraction of the drug in controlled-release, slow-release, programmed-release, timed-release, pulse-release, sustained-release or extended-release form in an amount of about 10 mg to about 400 mg, this composition providing, upon a single administration of 1 to about 4 dose units to a subject, (a) a $C_{max}$ greater than about 100 ng/ml, (b) a time to threshold concentration for therapeutic effect no longer than about 30 minutes and (c) a $T_{1/2}$ longer than about 9 h.

A preferred celecoxib composition provides, upon a single administration of 1 to about 4 dose units to a subject, (a) a $C_{max}$ greater than about 200 ng/ml, (b) a $T_{max}$ shorter than about 90 minutes, preferably shorter than about 60 minutes, (c) a blood serum concentration of at least 50 ng/ml, preferably at least 100 ng/ml, within about 15 minutes after such administration, and (d) a $T_{1/2}$ such that blood serum concentration remains above about 50 ng/ml, preferably above about 100 ng/ml, for at least 18 h, preferably for about 24 h, after such administration. It is preferred that the blood serum concentration should decline to a low level around or shortly after 24 h following administration, in other words that the composition provide a clearance time for the drug consistent with once-a-day administration.

A preferred composition has pharmacokinetic properties sufficient to provide rapid onset of therapeutic effect within about 1 h, and a duration of therapeutic effect of about 24 h, after oral administration thereof to a subject having a COX-2 mediated disorder.

A particularly preferred composition has the first fraction of the drug in an immediate-release form and the second fraction of the drug in a pulse-release form that releases a pulse of the drug about 8 h to about 12 h after administration. Such a composition is of especial utility for treatment of conditions such as osteoarthritis. For example, administration of such a composition at bedtime provides rapid onset of pain relief and enables pain-free sleep, and the pulse-release characteristic is timed to provide reduction in morning stiffness.

The weight ratio of the first to the second fraction of the drug in a composition of the invention is about 1:10 to about 10:1, preferably about 1:5 to about 5:1, for example about 1:1 or about 1:2.

Patent and other literature relating to nanoparticulate drug compositions teaches that, in general, the smaller the drug particle size, the greater is the advantage in speed of onset of therapeutic effect, or other pharmacodynamic benefit, obtained upon oral administration. For example, at least the following patents propose reduction of particle size to about 400 nm or smaller.

Above-cited U.S. Pat. No. 5,145,684.
Above-cited U.S. Pat. No. 5,298,262.
Above-cited U.S. Pat. No. 5,302,401.
Above-cited U.S. Pat. No. 5,336,507.
Above-cited U.S. Pat. No. 5,340,564.
Above-cited U.S. Pat. No. 5,346,702.
Above-cited U.S. Pat. No. 5,352,459.
Above-cited U.S. Pat. No. 5,429,824.
Above-cited U.S. Pat. No. 5,503,723.
Above-cited U.S. Pat. No. 5,510,118.
Above-cited U.S. Pat. No. 5,534,270.
Above-cited U.S. Pat. No. 5,552,160.
Above-cited U.S. Pat. No. 5,573,783.
Above-cited U.S. Pat. No. 5,585,108.
Above-cited U.S. Pat. No. 5,591,456.
Above-cited U.S. Pat. No. 5,662,883.
Above-cited U.S. Pat. No. 5,665,331.

In general, however, the smaller the drug particle size, the more grinding or milling time, energy and labor is required to produce the particles and consequently, the more costly and less efficient is the process. Thus, smaller nano-sized drug particles are generally significantly more expensive and labor-intensive to produce in quantity than larger nano-sized drug particles.

Surprisingly, we have discovered that a selective COX-2 inhibitory drug composition having a weight average particle size of about 0.45 µm to about 5 µm (referred to herein as a "peri-micron" formulation and particle size) exhibits onset time and bioavailability substantially equal to that of a comparative composition having a weight average particle size of about 0.2 µm to about 0.4 µM, as measured in vitro and in vivo. The peri-micron formulation requires less milling time and energy than the formulation comprising smaller nanoparticles with a weight average particle size in the 0.2–0.4 µm range.

It is further contemplated that certain advantages in addition to cost saving are obtainable with peri-micron as opposed to smaller particle sizes. For example, in situations where ultra-fine particles tend to agglomerate or fail to disperse in the gastrointestinal fluid, the slightly larger peri-micron particles can exhibit enhanced dispersion.

Accordingly, in a particularly preferred embodiment of the present invention, the immediate-release fraction of the selective COX-2 inhibitory drug is present in solid particles having a $D_{50}$ particle size of about 0.45 µm to about 5 µm, the immediate-release fraction providing at least a substantially similar $C_{max}$ and/or at most a substantially similar $T_{max}$ by comparison with an otherwise similar composition having an immediate-release fraction with a $D_{50}$ particle size of less than 0.4 µm, and/or providing a substantially greater $C_{max}$ and/or a substantially shorter $T_{max}$ by comparison with an otherwise similar composition having an immediate release fraction with a $D_{50}$ particle size larger than 1.0 µm.

In one aspect of this embodiment, the immediate-release fraction has a $D_{25}$ particle size of about 0.45 µm to about 1 µm, preferably a $D_{50}$ particle size of about 0.45 µm to about 1 µm, for example about 0.5 µm to about 0.9 µm.

A composition of the invention can be a substantially homogeneous flowable mass such as a particulate or granular solid or a liquid, or it can be in the form of discrete articles such as capsules or tablets each comprising a single dose unit.

In a composition that is a substantially homogeneous flowable mass, single dose units are measurably removable using a suitable volumetric measuring device such as a spoon or cup. Suitable flowable masses include, but are not limited to, powders and granules. Alternatively, the flowable mass can be a fluid suspension as described above. In preparing such a suspension, use of a wetting agent such as polysorbate 80 is likely to be beneficial. A suspension can be prepared by dispersing the drug in nanoparticulate and/or microparticulate form in the liquid phase; alternatively the particulate drug can be precipitated from solution in a solvent such as an alcohol, preferably ethanol. The liquid phase preferably comprises a palatable vehicle such as water, syrup or fruit juice, for example apple juice.

The selective COX-2 inhibitory drug can be any such drug known in the art, including without limitation compounds disclosed in the patents and publications listed below, each of which is individually incorporated herein by reference.

U.S. Pat. No. 5,344,991 to Reitz & Li.
U.S. Pat. No. 5,380,738 to Norman et al.
U.S. Pat. No. 5,393,790 to Reitz et al.
U.S. Pat. No. 5,401,765 to Lee.
U.S. Pat. No. 5,418,254 to Huang & Reitz.
U.S. Pat. No. 5,420,343 to Koszyk & Weier.
U.S. Pat. No. 5,434,178 to Talley & Rogier.
U.S. Pat. No. 5,436,265 to Black et al.
Above-cited U.S. Pat. No. 5,466,823.
U.S. Pat. No. 5,474,995 to Ducharme et al.
U.S. Pat. No. 5,475,018 to Lee & Bertenshaw.
U.S. Pat. No. 5,486,534 to Lee et al.
U.S. Pat. No. 5,510,368 to Lau et al.
U.S. Pat. No. 5,521,213 to Prasit et al.
U.S. Pat. No. 5,536,752 to Ducharme et al.
U.S. Pat. No. 5,543,297 to Cromlish et al.
U.S. Pat. No. 5,547,975 to Talley et al.
U.S. Pat. No. 5,550,142 to Ducharme et al.
U.S. Pat. No. 5,552,422 to Gauthier et al.
U.S. Pat. No. 5,585,504 to Desmond et al.
U.S. Pat. No. 5,593,992 to Adams et al.
U.S. Pat. No. 5,596,008 to Lee.
U.S. Pat. No. 5,604,253 to Lau et al.
U.S. Pat. No. 5,604,260 to Guay & Li.
U.S. Pat. No. 5,616,458 to Lipsky et al.
U.S. Pat. No. 5,616,601 to Khanna et al.
U.S. Pat. No. 5,620,999 to Weier et al.
Above-cited U.S. Pat. No. 5,633,272.
U.S. Pat. No. 5,639,780 to Lau et al.
U.S. Pat. No. 5,643,933 to Talley et al.
U.S. Pat. No. 5,658,903 to Adams et al.
U.S. Pat. No. 5,668,161 to Talley et al.
U.S. Pat. No. 5,670,510 to Huang & Reitz.
U.S. Pat. No. 5,677,318 to Lau.
U.S. Pat. No. 5,681,842 to Dellaria & Gane.
U.S. Pat. No. 5,686,460 to Nicolaï et al.
U.S. Pat. No. 5,686,470 to Weier et al.
U.S. Pat. No. 5,696,143 to Talley et al.
U.S. Pat. No. 5,710,140 to Ducharme et al.
U.S. Pat. No. 5,716,955 to Adams et al.
U.S. Pat. No. 5,723,485 to Güngör & Teulon.

U.S. Pat. No. 5,739,166 to Reitz et al.
U.S. Pat. No. 5,741,798 to Lazer et al.
U.S. Pat. No. 5,756,499 to Adams et al.
U.S. Pat. No. 5,756,529 to Isakson & Talley.
U.S. Pat. No. 5,776,967 to Kreft et al.
U.S. Pat. No. 5,783,597 to Beers & Wachter.
U.S. Pat. No. 5,789,413 to Black et al.
U.S. Pat. No. 5,807,873 to Nicolai & Teulon.
U.S. Pat. No. 5,817,700 to Dube et al.
U.S. Pat. No. 5,830,911 to Failli et al.
U.S. Pat. No. 5,849,943 to Atkinson & Wang.
U.S. Pat. No. 5,859,036 to Sartori et al.
U.S. Pat. No. 5,861,419 to Dube et al.
U.S. Pat. No. 5,866,596 to Sartori & Teulon.
U.S. Pat. No. 5,869,524 to Failli.
U.S. Pat. No. 5,869,660 to Adams et al.
U.S. Pat. No. 5,883,267 to Rossen et al.
U.S. Pat. No. 5,892,053 to Zhi et al.
U.S. Pat. No. 5,922,742 to Black et al.
U.S. Pat. No. 5,929,076 to Adams & Garigipati.
U.S. Pat. No. 5,932,598 to Talley et al.
U.S. Pat. No. 5,935,990 to Khanna et al.
U.S. Pat. No. 5,945,539 to Haruta et al.
U.S. Pat. No. 5,958,978 to Yamazaki et al.
U.S. Pat. No. 5,968,958 to Guay et al.
U.S. Pat. No. 5,972,950 to Nicolaï & Teulon.
U.S. Pat. No. 5,973,191 to Mamett & Kalgutkar.
U.S. Pat. No. 5,981,576 to Belley et al.
U.S. Pat. No. 5,994,381 to Haruta et al.
U.S. Pat. No. 6,002,014 to Haruta et al.
U.S. Pat. No. 6,004,960 to Li et al.
U.S. Pat. No. 6,005,000 to Hopper et al.
U.S. Pat. No. 6,020,343 to Belley et al.
U.S. Pat. No. 6,020,347 to DeLaszlo & Hagmann.
U.S. Pat. No. 6,034,256 to Carter et al.
U.S. Pat. No. 6,040,319 to Corley et al.
U.S. Pat. No. 6,040,450 to Davies et al.
U.S. Pat. No. 6,046,208 to Adams et al.
U.S. Pat. No. 6,046,217 to Friesen et al.
U.S. Pat. No. 6,057,319 to Black et al.
U.S. Pat. No. 6,063,804 to De Nanteuil et al.
U.S. Pat. No. 6,063,807 to Chabrier de Lassauniere & Broquet.
U.S. Pat. No. 6,071,954 to LeBlanc et al.
U.S. Pat. No. 6,077,868 to Cook et al.
U.S. Pat. No. 6,077,869 to Sui & Wachter.
U.S. Pat. No. 6,083,969 to Ferro et al.
U.S. Pat. No. 6,096,753 to Spohr et al.
U.S. Pat. No. 6,133,292 to Wang et al.
International Patent Publication No. WO 94/15932.
International Patent Publication No. WO 96/19469.
International Patent Publication No. WO 96/26921.
International Patent Publication No. WO 96/31509.
International Patent Publication No. WO 96/36623.
International Patent Publication No. WO 96/38418.
International Patent Publication No. WO 97/03953.
International Patent Publication No. WO 97/10840.
International Patent Publication No. WO 97/13755.
International Patent Publication No. WO 97/13767.
International Patent Publication No. WO 97/25048.
International Patent Publication No. WO 97/30030.
International Patent Publication No. WO 97/34882.
International Patent Publication No. WO 97/46524.
International Patent Publication No. WO 98/04527.
International Patent Publication No. WO 98/06708.
International Patent Publication No. WO 98/07425.
International Patent Publication No. WO 98/17292.
International Patent Publication No. WO 98/21195.
International Patent Publication No. WO 98/22457.
International Patent Publication No. WO 98/32732.
International Patent Publication No. WO 98/41516.
International Patent Publication No. WO 98/43966.
International Patent Publication No. WO 98/45294.
International Patent Publication No. WO 98/47871.
International Patent Publication No. WO 99/01130.
International Patent Publication No. WO 99/01131.
International Patent Publication No. WO 99/01452.
International Patent Publication No. WO 99/01455.
International Patent Publication No. WO 99/10331.
International Patent Publication No. WO 99/10332.
International Patent Publication No. WO 99/11605.
International Patent Publication No. WO 99/12930.
International Patent Publication No. WO 99/14195.
International Patent Publication No. WO 99/14205.
International Patent Publication No. WO 99/15505.
International Patent Publication No. WO 99/23087.
International Patent Publication No. WO 99/24404.
International Patent Publication No. WO 99/25695.
International Patent Publication No. WO 99/35130.
International Patent Publication No. WO 99/61016.
International Patent Publication No. WO 99/61436.
International Patent Publication No. WO 99/62884.
International Patent Publication No. WO 99/64415.
International Patent Publication No. WO 00/01380.
International Patent Publication No. WO 00/08024.
International Patent Publication No. WO 00/10993.
International Patent Publication No. WO 00/13684.
International Patent Publication No. WO 00/18741.
International Patent Publication No. WO 00/18753.
International Patent Publication No. WO 00/23426.
International Patent Publication No. WO 00/24719.
International Patent Publication No. WO 00/26216.
International Patent Publication No. WO 00/31072.
International Patent Publication No. WO 00/40087.
International Patent Publication No. WO 00/56348.
European Patent Application No. 0 799 823.
European Patent Application No. 0 846 689.
European Patent Application No. 0 863 134.
European Patent Application No. 0 985 666.

Compositions of the invention are especially useful for compounds having the formula (VI):

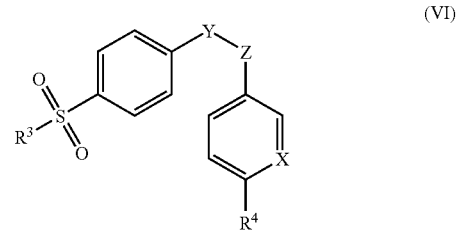

where $R^3$ is a methyl or amino group, $R^4$ is hydrogen or a $C_{1-4}$ alkyl or alkoxy group, X is N or $CR^5$ where $R^5$ is hydrogen or halogen, and Y and Z are independently carbon or nitrogen atoms defining adjacent atoms of a five- to six-membered ring that is unsubstituted or substituted at one or more positions with oxo, halo, methyl or halomethyl groups. Preferred such five- to six-membered rings are cyclopentenone, furanone, methylpyrazole, isoxazole and pyridine rings substituted at no more than one position.

Illustratively, compositions of the invention are suitable for celecoxib, deracoxib, valdecoxib, rofecoxib, 5-chloro-3-(4-methylsulfonyl)phenyl-2-(2-methyl-5-pyridinyl)pyridine, 2-(3,5-difluorophenyl)-3-[4-(methylsulfonyl)phenyl]-2-cyclopenten-1-one and (S)-6,8-dichloro-2-(trifluoromethyl)-2H-1-benzopyran-3-carboxylic acid, more particularly celecoxib and valdecoxib, and most particularly celecoxib.

The invention is illustrated herein with particular reference to celecoxib, and it will be understood that any other selective COX-2 inhibitory compound of low solubility in water can, if desired, be substituted in whole or in part for celecoxib in compositions herein described.

Compositions of the invention are useful in treatment and prevention of a very wide range of disorders mediated by COX-2, including but not restricted to disorders characterized by inflammation, pain and/or fever. Such compositions are especially useful as anti-inflammatory agents, such as in treatment of arthritis, with the additional benefit of having significantly less harmful side effects than compositions of conventional nonsteroidal anti-inflammatory drugs (NSAIDs) that lack selectivity for COX-2 over COX-1. In particular, compositions of the invention have reduced potential for gastrointestinal toxicity and gastrointestinal irritation including upper gastrointestinal ulceration and bleeding, reduced potential for renal side effects such as reduction in renal function leading to fluid retention and exacerbation of hypertension, reduced effect on bleeding times including inhibition of platelet function, and possibly a lessened ability to induce asthma attacks in aspirin-sensitive asthmatic subjects, by comparison with compositions of conventional NSAIDs. Thus compositions of the invention are particularly useful as an alternative to conventional NSAIDs where such NSAIDs are contraindicated, for example in patients with peptic ulcers, gastritis, regional enteritis, ulcerative colitis, diverticulitis or with a recurrent history of gastrointestinal lesions; gastrointestinal bleeding, coagulation disorders including anemia such as hypoprothrombinemia, hemophilia or other bleeding problems; kidney disease; or in patients prior to surgery or patients taking anticoagulants.

Contemplated compositions are useful to treat a variety of arthritic disorders, including but not limited to rheumatoid arthritis, spondyloarthropathies, gouty arthritis, osteoarthritis, systemic lupus erythematosus and juvenile arthritis.

Such compositions are useful in treatment of asthma, bronchitis, menstrual cramps, preterm labor, tendinitis, bursitis, allergic neuritis, cytomegalovirus infectivity, apoptosis including HIV-induced apoptosis, lumbago, liver disease including hepatitis, skin-related conditions such as psoriasis, eczema, acne, burns, dermatitis and ultraviolet radiation damage including sunburn, and post-operative inflammation including that following ophthalmic surgery such as cataract surgery or refractive surgery.

Such compositions are useful to treat gastrointestinal conditions such as inflammatory bowel disease, Crohn's disease, gastritis, irritable bowel syndrome and ulcerative colitis.

Such compositions are useful in treating inflammation in such diseases as migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like.

Such compositions are useful in treatment of ophthalmic diseases, such as retinitis, conjunctivitis, retinopathies, uveitis, ocular photophobia, and of acute injury to the eye tissue.

Such compositions are useful in treatment of pulmonary inflammation, such as that associated with viral infections and cystic fibrosis, and in bone resorption such as that associated with osteoporosis.

Such compositions are useful for treatment of certain central nervous system disorders, such as cortical dementias including Alzheimer's disease, neurodegeneration, and central nervous system damage resulting from stroke, ischemia and trauma. The term "treatment" in the present context includes partial or total inhibition of dementias, including Alzheimer's disease, vascular dementia, multi-infarct dementia, pre-senile dementia, alcoholic dementia and senile dementia.

Such compositions are useful in treatment of allergic rhinitis, respiratory distress syndrome, endotoxin shock syndrome and liver disease.

Such compositions are useful in treatment of pain, including but not limited to postoperative pain, dental pain, muscular pain, and pain resulting from cancer. For example, such compositions are useful for relief of pain, fever and inflammation in a variety of conditions including rheumatic fever, influenza and other viral infections including common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, and trauma following surgical and dental procedures.

Such compositions are useful for treating and preventing inflammation-related cardiovascular disorders, including vascular diseases, coronary artery disease, aneurysm, vascular rejection, arteriosclerosis, atherosclerosis including cardiac transplant atherosclerosis, myocardial infarction, embolism, stroke, thrombosis including venous thrombosis, angina including unstable angina, coronary plaque inflammation, bacterial-induced inflammation including Chlamydia-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries.

Such compositions are useful in treatment of angiogenesis-related disorders in a subject, for example to inhibit tumor angiogenesis. Such compositions are useful in treatment of neoplasia, including metastasis; ophthalmological conditions such as corneal graft rejection, ocular neovascularization, retinal neovascularization including neovascularization following injury or infection, diabetic retinopathy, macular degeneration, retrolental fibroplasia and neovascular glaucoma; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis.

Such compositions are useful in prevention and treatment of benign and malignant tumors and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers that effect epithelial cells throughout the body. Neoplasias for which compositions of the invention are contemplated to be particularly useful are gastrointestinal cancer, Barrett's esophagus, liver cancer, bladder cancer, pancreatic cancer, ovarian cancer, prostate cancer, cervical cancer, lung cancer, breast cancer and skin cancer. Such compositions can also be used to treat fibrosis that occurs with radiation therapy. Such compositions can be used to treat subjects having adenomatous polyps, including those with familial adenomatous polyposis (FAP). Additionally, such compositions can be used to prevent polyps from forming in patients at risk of FAP.

Such compositions inhibit prostanoid-induced smooth muscle contraction by inhibiting synthesis of contractile prostanoids and hence can be of use in treatment of dysmenorrhea, premature labor, asthma and eosinophil-related disorders. They also can be of use for decreasing bone loss particularly in postmenopausal women (i.e., treatment of osteoporosis), and for treatment of glaucoma.

Preferred uses for compositions of the invention are for treatment of rheumatoid arthritis and osteoarthritis, for pain management generally (particularly post-oral surgery pain, post-general surgery pain, post-orthopedic surgery pain, and acute flares of osteoarthritis), for treatment of Alzheimer's disease, and for colon cancer chemoprevention.

For treatment of rheumatoid arthritis or osteoarthritis, compositions of the invention can be used to provide a daily dosage of celecoxib of about 50 mg to about 1000 mg, preferably about 100 mg to about 600 mg, more preferably about 150 mg to about 500 mg, still more preferably about 175 mg to about 400 mg, for example about 200 mg. A daily dose of celecoxib of about 0.7 to about 13 mg/kg body weight, preferably about 1.3 to about 8 mg/kg body weight, more preferably about 2 to about 6.7 mg/kg body weight, and still more preferably about 2.3 to about 5.3 mg/kg body weight, for example about 2.7 mg/kg body weight, is generally appropriate when administered in a composition of the invention. The daily dose can be administered in one to about four doses per day, preferably one or two doses per day.

For treatment of Alzheimer's disease or cancer, compositions of the invention can be used to provide a daily dosage of celecoxib of about 50 mg to about 1000 mg, preferably about 100 mg to about 800 mg, more preferably about 150 mg to about 600 mg, and still more preferably about 175 mg to about 400 mg, for example about 400 mg. A daily dose of about 0.7 to about 13 mg/kg body weight, preferably about 1.3 to about 10.7 mg/kg body weight, more preferably about 2 to about 8 mg/kg body weight, and still more preferably about 2.3 to about 5.3 mg/kg body weight, for example about 5.3 mg/kg body weight, is generally appropriate when administered in a composition of the invention. The daily dose can be administered in one to about four doses per day, preferably one or two doses per day.

For pain management, compositions of the invention can be used to provide a daily dosage of celecoxib of about 50 mg to about 1000 mg, preferably about 100 mg to about 600 mg, more preferably about 150 mg to about 500 mg, and still more preferably about 175 mg to about 400 mg, for example about 200 mg. A daily dose of celecoxib of about 0.7 to about 13 mg/kg body weight, preferably about 1.3 to about 8 mg/kg body weight, more preferably about 2 to about 6.7 mg/kg body weight, and still more preferably about 2.3 to about 5.3 mg/kg body weight, for example about 2.7 mg/kg body weight, is generally appropriate when administered in a composition of the invention. The daily dose can be administered in one to about four doses per day. Administration at a rate of one 50 mg dose unit four times a day, one 100 mg dose unit or two 50 mg dose units twice a day or one 200 mg dose unit, two 100 mg dose units or four 50 mg dose units once a day is preferred.

For selective COX-2 inhibitory drugs other than celecoxib, appropriate doses can be selected by reference to the patent literature cited hereinabove.

Besides being useful for human treatment, compositions of the invention are useful for veterinary treatment of companion animals, exotic animals, farm animals, and the like, particularly mammals. More particularly, compositions of the invention are useful for treatment of COX-2 mediated disorders in horses, dogs and cats.

The present invention is further directed to a therapeutic method of treating a condition or disorder where treatment with a COX-2 inhibitory drug is indicated, the method comprising oral administration of a composition of the invention to a subject in need thereof. The dosage regimen to prevent, give relief from, or ameliorate the condition or disorder preferably corresponds to once-a-day or twice-a-day treatment, but can be modified in accordance with a variety of factors. These include the type, age, weight, sex, diet and medical condition of the subject and the nature and severity of the disorder. Thus, the dosage regimen actually employed can vary widely and can therefore deviate from the preferred dosage regimens set forth above.

Initial treatment can begin with a dose regimen as indicated above. Treatment is generally continued as necessary over a period of several weeks to several months or years until the condition or disorder has been controlled or eliminated. Subjects undergoing treatment with a composition of the invention can be routinely monitored by any of the methods well known in the art to determine effectiveness of therapy. Continuous analysis of data from such monitoring permits modification of the treatment regimen during therapy so that optimally effective doses are administered at any point in time, and so that the duration of treatment can be determined. In this way, the treatment regimen and dosing schedule can be rationally modified over the course of therapy so that the lowest amount of the composition exhibiting satisfactory effectiveness is administered, and so that administration is continued only for so long as is necessary to successfully treat the condition or disorder.

By virtue of the rapid onset of therapeutic effect exhibited by compositions of the invention, these compositions have particular advantages over prior formulations of celecoxib for treatment of acute COX-2 mediated disorders, especially for the relief of pain. At the same time, by virtue of the long duration of therapeutic effect exhibited by compositions of the invention, these compositions have particular advantages over prior formulations of celecoxib for treatment of chronic COX-2 mediated disorders, where once-a-day treatment is especially desirable. Compositions of the invention are uniquely advantageous where a combination of rapid onset and long duration of therapeutic effect is required.

The present compositions can be used in combination therapies with opioids and other analgesics, including narcotic analgesics, Mu receptor antagonists, Kappa receptor antagonists, non-narcotic (i.e. non-addictive) analgesics, monoamine uptake inhibitors, adenosine regulating agents, cannabinoid derivatives, Substance P antagonists, neurokinin-1 receptor antagonists and sodium channel blockers, among others. Preferred combination therapies comprise use of a composition of the invention with one or more compounds selected from aceclofenac, acemetacin, e-acetamidocaproic acid, acetaminophen, acetaminosalol, acetanilide, acetylsalicylic acid (aspirin), S-adenosylmethionine, alclofenac, alfentanil, allylprodine, alminoprofen, aloxiprin, alphaprodine, aluminum bis(acetylsalicylate), amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antipyrine salicylate, antrafenine, apazone, bendazac, benorylate, benoxaprofen, benzpiperylon, benzydamine, benzylmorphine, bermoprofen, bezitramide, α-bisabolol, bromfenac, p-bromoacetanilide, 5-bromosalicylic acid acetate, bromosaligenin, bucetin, bucloxic acid, bucolome, bufexamac, bumadizon, buprenorphine, butacetin, butibufen, butophanol, calcium acetylsalicylate, carbamazepine, carbiphene, carprofen, carsalam, chlorobutanol, chlorthenoxazin, choline salicylate, cinchophen, cinmetacin, ciramadol, clidanac, clometacin, clonitazene, clonixin, clopirac, clove, codeine, codeine methyl bromide, codeine phosphate, codeine sulfate, cropropamide, crotethamide, desomorphine, dexoxadrol, dextromoramide, dezocine, diampromide, diclofenac sodium, difenamizole, difenpiramide, diflunisal, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, flufenamic acid, flunoxaprofen, fluoresone, flupirtine, fluproquazone, flurbiprofen, fosfosal, gentisic acid, glafenine, glucametacin, glycol salicylate, guaiazulene, hydrocodone, hydromorphone, hydroxypethidine, ibufenac, ibuprofen, ibuproxam, imidazole salicylate, indomethacin, indoprofen, isofezolac, isoladol, isomethadone, isonixin, isoxepac, isoxicam, ketobemidone, ketoprofen, ketorolac, p-lactophenetide, lefetamine, levorphanol, lofentanil, lonazolac, lomoxicam, loxoprofen, lysine acetylsalicylate, magnesium acetylsalicylate, meclofenamic acid, mefenamic acid, meperidine, meptazinol, mesalamine, metazocine, methadone hydrochloride, methotrimeprazine, metiazinic acid, metofoline, metopon, mofebutazone, mofezolac, morazone, morphine, morphine hydrochloride, morphine sulfate, morpholine salicylate, myrophine, nabumetone, nalbuphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paranyline, parsalmide, pentazocine, perisoxal, phenacetin, phenadoxone, phenazocine, phenazopyridine hydrochloride, phenocoll, phenoperidine, phenopyrazone, phenyl acetylsalicylate, phenylbutazone, phenyl salicylate, phenyramidol, piketoprofen, piminodine, pipebuzone, piperylone, piprofen, pirazolac, piritramide, piroxicam, pranoprofen, proglumetacin, proheptazine, promedol, propacetamol, propiram, propoxyphene, propyphenazone, proquazone, protizinic acid, ramifenazone, remifentanil, rimazolium metilsulfate, salacetamide, salicin, salicylamide, salicylamide o-acetic acid, salicylsulfuric acid, salsalte, salverine, simetride, sodium salicylate, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tolfenamic acid, tolmetin, tramadol, tropesin, viminol, xenbucin, ximoprofen, zaltoprofen and zomepirac (see *The Merck Index*, 12th Edition (1996), Therapeutic Category and Biological Activity Index, lists therein headed "Analgesic", "Anti-inflammatory" and "Antipyretic").

Particularly preferred combination therapies comprise use of a composition of the invention with an opioid compound, more particularly where the opioid compound is codeine, meperidine, morphine or a derivative thereof.

The compound to be administered in combination with a selective COX-2 inhibitory drug can be formulated separately from the drug or co-formulated with the drug in a composition of the invention. Where a selective COX-2 inhibitory drug is co-formulated with a second drug, for example an opioid drug, the second drug can be formulated in immediate-release, rapid-onset, sustained-release or dual-release form.

A dose unit containing a particular amount of a selective COX-2 inhibitory drug, preferably celecoxib, can be selected to accommodate any desired frequency of administration used to achieve a desired daily dosage. The daily dosage and frequency of administration, and therefore the selection of an appropriate dose unit, depends on a variety of factors, including the age, weight, sex and medical condition of the subject, and the nature and severity of the condition or disorder, and thus may vary widely.

The composition preferably contains about 1% to about 95%, preferably about 10% to about 90%, more preferably about 25% to about 85%, and still more preferably about 30% to about 80%, by weight of the selective COX-2 inhibitory drug.

A composition of the invention is preferably made in the form of discrete dose units each containing a predetermined amount of the selective COX-2 inhibitory drug, such as tablets, pills, hard or soft capsules, lozenges, cachets, dispensable powders, granules, suspensions, elixirs or other liquids, or any other form reasonably adapted for oral administration. Tablets, pills and the like additionally can be prepared with or without coatings.

Compositions of the invention suitable for buccal or sublingual administration include, for example, lozenges comprising a selective COX-2 inhibitory drug in a flavored base, such as sucrose, and acacia or tragacanth, and pastilles comprising celecoxib in an inert base such as gelatin and glycerin or sucrose and acacia.

Liquid dosage forms for oral administration include pharmaceutically acceptable suspensions, syrups, and elixirs containing inert diluents commonly used in the art, such as water. Such compositions may also comprise, for example, wetting agents, emulsifying and suspending agents, and sweetening, flavoring, and perfuming agents.

Excipients useful in compositions of the invention can be liquids, semi-solids, solids or combinations thereof. Excipient-containing compositions of the invention can be prepared by any suitable method of pharmacy which includes the step of bringing into association one or more excipients with the selective COX-2 inhibitory drug, in a combination of dissolved, suspended, nanoparticulate, microparticulate or controlled-release, slow-release, programmed-release, timed-release, pulse-release, sustained-release or extended-release forms thereof. In general, such compositions are prepared by uniformly and intimately admixing the drug with a liquid or finely divided diluent, or both, and then, if necessary or desired, encapsulating or shaping the product. For example, a tablet can be prepared by compressing or molding a powder or granules of a selective COX-2 inhibitory drug, together with one or more excipients. Compressed tablets can be prepared by compressing, in a suitable machine, a free-flowing composition, such as a powder or granules, comprising the drug optionally mixed with one or more binding agent(s), lubricant(s), inert diluent(s), wetting agent(s) and/or dispersing agent(s). Molded tablets can be made by molding, in a suitable machine, the drug moistened with an inert liquid diluent.

Compositions of the invention typically comprise a selective COX-2 inhibitory drug in a desired amount admixed with one or more excipients selected from the group consisting of pharmaceutically acceptable diluents, disintegrants, binding agents, adhesives, wetting agents, lubricants, and anti-adherent agents. In addition, nanoparticles, microparticles and/or controlled-release, slow-release, programmed-release, timed-release, pulse-release, sustained-release or extended-release particles of the drug, if present, can optionally contain one or more matrix polymers and/or surface modifying agents. Drug particles can be aggregated into beads which are enveloped in a coating conferring controlled-release, slow-release, programmed-release, timed-release, pulse-release, sustained-release or extended-release properties to the drug in such beads.

Through selection and combination of excipients, compositions can be provided exhibiting improved performance with respect to, among other properties, efficacy, bioavailability, clearance time, stability, compatibility of drug and excipients, safety, dissolution profile, disintegration profile and/or other pharmacokinetic, Chemical and/or physical properties. Where the composition is formulated as a tablet, the combination of excipients selected provides tablets that can exhibit improvement, among other properties, in dissolution profile, hardness, crushing strength, and/or friability.

Compositions of the invention optionally comprise one or more pharmaceutically acceptable diluents as excipients. Suitable diluents illustratively include, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of α- and amorphous cellulose (e.g., Rexcel™) and powdered cellulose; calcium carbonate; glycine; bentonite; polyvinylpyrrolidone; and the like. Such diluents, if present, constitute in total about 5% to about 99%, preferably about 10% to about 85%, and more preferably about 20% to about 80%, of the total weight of the composition. The diluent or diluents selected preferably exhibit suitable flow properties and, where tablets are desired, compressibility.

Lactose and microcrystalline cellulose, either individually or in combination, are preferred diluents. Both diluents are chemically compatible with celecoxib. The use of extragranular microcrystalline cellulose (that is, microcrystalline cellulose added to a wet granulated composition after a drying step) can be used to improve hardness (for tablets) and/or disintegration time. Lactose, especially lactose monohydrate, is particularly preferred. Lactose typically provides compositions having suitable release rates of celecoxib, stability, pre-compression flowability, and/or drying properties at a relatively low diluent cost. It provides a high density substrate that aids densification during granulation (where wet granulation is employed) and therefore improves blend flow properties.

Compositions of the invention optionally comprise one or more pharmaceutically acceptable disintegrants as excipients, particularly for tablet formulations. Suitable disintegrants include, either individually or in combination, starches, including sodium starch glycolate (e.g., Explotab™ of PenWest) and pregelatinized corn starches (e.g., National™ 1551, National™ 1550, and Colorcon™ 1500), clays (e.g., Veegum™ HV), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, constitute in total about 0.2% to about 30%, preferably about 0.2% to about 10%, and more preferably about 0.2% to about 5%, of the total weight of the composition.

Croscarmellose sodium is a preferred disintegrant for tablet or capsule disintegration, and, if present, preferably constitutes about 0.2% to about 10%, more preferably about 0.2% to about 7%, and still more preferably about 0.2% to about 5%, of the total weight of the composition. Croscarmellose sodium confers superior intragranular disintegration capabilities to granulated compositions of the present invention.

Compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™); and ethylcellulose (e.g., Ethocel™). Such binding agents and/or adhesives, if present, constitute in total about 0.5% to about 25%, preferably about 0.75% to about 15%, and more preferably about 1% to about 10%, of the total weight of the composition.

Compositions of the invention optionally comprise one or more pharmaceutically acceptable wetting agents as excipients. Such wetting agents are preferably selected to maintain the selective COX-2 inhibitory drug in close association with water, a condition that is believed to improve bioavailability of the composition.

Non-limiting examples of surfactants that can be used as wetting agents in compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefossé), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefossé), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, preferably about 0.4% to about 10%, and more preferably about 0.5% to about 5%, of the total weight of the composition.

Wetting agents that are anionic surfactants are preferred. Sodium lauryl sulfate is a particularly preferred wetting agent. Sodium lauryl sulfate, if present, constitutes about 0.25% to about 7%, more preferably about 0.4% to about 4%, and still more preferably about 0.5% to about 2%, of the total weight of the composition.

Compositions of the invention optionally comprise one or more pharmaceutically acceptable lubricants (including anti-adherents and/or glidants) as excipients. Suitable lubricants include, either individually or in combination, glyceryl behapate (e.g., Compritol™ 888); stearic acid and salts thereof, including magnesium, calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, preferably about 0.2% to about 8%, and more preferably about 0.25% to about 5%, of the total weight of the composition.

Magnesium stearate is a preferred lubricant used, for example, to reduce friction between the equipment and granulated mixture during compression of tablet formulations.

Suitable anti-adherents include talc, cornstarch, DL-leucine, sodium lauryl sulfate and metallic stearates. Talc is a preferred anti-adherent or glidant used, for example, to reduce formulation sticking to equipment surfaces and also to reduce static in the blend. Talc, if present, constitutes about 0.1% to about 10%, more preferably about 0.25% to about 5%, and still more preferably about 0.5% to about 2%, of the total weight of the composition.

Other excipients such as colorants, flavors and sweeteners are known in the pharmaceutical art and can be used in compositions of the present invention. Tablets can be coated, for example with an enteric coating, or uncoated. Compositions of the invention can further comprise, for example, buffering agents.

Optionally, one or more effervescent agents can be used as disintegrants and/or to enhance organoleptic properties of compositions of the invention. When present in compositions of the invention to promote dosage form disintegration, one or more effervescent agents are preferably present in a total amount of about 30% to about 75%, and preferably about 45% to about 70%, for example about 60%, by weight of the composition.

Although unit dose hard capsule and tablet compositions of the invention can be prepared, for example, by direct encapsulation or direct compression, they preferably are wet granulated prior to encapsulation or compression. Wet granulation, among other effects, densifies milled compositions resulting in improved flow properties, improved compression characteristics and easier metering or weight dispensing of the compositions for encapsulation or tableting. The secondary particle size resulting from granulation (i.e., granule size) is not narrowly critical, it being important only that the average granule size preferably is such as to allow for convenient handling and processing and, for tablets, to permit the formation of a directly compressible mixture that forms pharmaceutically acceptable tablets.

The desired tap and bulk densities of the granules are normally about 0.3 g/ml to about 1.0 g/ml.

For tablet formulations, the complete mixture in an amount sufficient to make a uniform batch of tablets is subjected to tableting in a conventional production scale tableting machine at normal compression pressure (for example, applying a force of about 1 kN to about 50 kN in a typical tableting die). Any tablet hardness convenient with respect to handling, manufacture, storage and ingestion may be employed. For 100 mg tablets, hardness is preferably at least 4 kP, more preferably at least about 5 kP, and still more preferably at least about 6 kP. For 200 mg tablets, hardness is preferably at least 7 kP, more preferably at least about 9 kP, and still more preferably at least about 11 IkP. The mixture, however, is not to be compressed to such a degree that there is subsequent difficulty in achieving hydration when exposed to gastric fluid.

For tablet formulations, tablet friability preferably is less than about 1.0%, more preferably less than 0.8%, and still more preferably less than about 0.5% in a standard test.

The first and second fractions of the selective COX-2 inhibitory drug can be intimately coformulated, for example within individual granules that are subsequently encapsulated or compressed into tablets. Alternatively, the first and second fractions can be spatially separated in a composition of the invention. Illustratively, within a single hard capsule there can be separate granules or beads, for example coated beads, containing the drug in immediate-release form or in controlled-release, slow-release, programmed-release, timed-release, pulse-release, sustained-release or extended-release form. Within a single unit dose tablet there can be separate layers containing the drug in immediate-release form or in controlled-release, slow-release, programmed release, timed-release, pulse-release, sustained-release or extended-release form. For example, a two-layer selective COX-2 inhibitory drug tablet similar to that described for naproxen in above-cited U.S. Pat. No. 5,609,884 can be prepared.

In a particularly preferred embodiment of the present invention, the second fraction of the selective COX-2 inhibitory drug is distributed in a sustained-release matrix comprising HPMC having a viscosity, 2% in water, of about 100 to about 8000 cP. Compositions of this embodiment of the invention are referred to for convenience herein as "dual-release matrix compositions". When formulated as tablets, which are a preferred dosage form for this embodiment, such compositions are referred to herein as "dual-release matrix tablets".

A matrix composition of the invention comprises HPMC in an amount sufficient to extend the release profile of the selective COX-2 inhibitory drug. Typically such an amount is about 0.1% to about 40%, preferably about 5% to about 30%, for example about 10%, of the composition by weight. Preferably the weight ratio of HPMC to the second fraction of selective COX-2 inhibitory drug is about 1:1 to about 1:12, more preferably about 1:1 to about 1:6.

HPMCs vary in the chain length of their cellulosic backbone. This directly affects the viscosity of an aqueous dispersion of the HPMC. Viscosity is normally measured at a 2% by weight concentration of the HPMC in water. HPMCs having viscosity, 2% in water, of less than about 100 cP can be useful, for example as binding agents, but tend not to have useful release-extending properties for medicaments. Such HPMCs are said to have good binding properties and less desirable sustaining properties. The term "binding properties" herein refers to suitability as a binding agent for tablet production by wet granulation, wherein, for example, HPMC is dissolved in water for spraying onto dry powders to be granulated. The term "sustaining properties" herein refers to suitability as a release-extending matrix. HPMCs with good sustaining properties are typically too viscous for use as a binding agent in wet granulation techniques. According to the present invention, the HPMC(s) used to form the release-extending matrix of a dual-release celecoxib composition should have a viscosity, 2% in water, of about 100 to about 8000 cP, preferably about 1000 to about 8000 cP, for example about 4000 cP.

HPMCs also vary in the degree of substitution of available hydroxyl groups on the cellulosic backbone by methoxyl groups and by hydroxypropoxyl groups. With increasing hydroxypropoxyl substitution, the resulting HPMC becomes more hydrophilic in nature. It is preferred in dual-release matrix compositions of the present invention to use HPMCs having about 15% to about 35%, more preferably about 19% to about 30%, and most preferably about 19% to about 24%, methoxyl substitution, and having about 3% to about 15%, more preferably about 4% to about 12%, and most preferably about 7% to about 12%, hydroxypropoxyl substitution.

HPMCs which are relatively hydrophilic in nature and are useful in compositions in the invention are illustratively available under the brand names Methocel™ of Dow Chemical Co. and Metolose™ of Shin-Etsu Chemical Co. Examples of HPMCs of a low viscosity grade, generally unsuitable in compositions of the present invention except as binding agents, include Methocel™ E5, Methocel™ E15 LV, Methocel™ E50 LV, Methocel™ K100 LV and Methocel™ F50 LV, whose 2% by weight aqueous solutions have viscosities of 5 cP, 15 cP, 50 cP, 100 cP and 50 cP, respectively. Examples of HPMCs having medium viscosity include Methocel™ E4M and Methocel™ K4M, 2% by weight aqueous solutions of each of which have a viscosity of 4000 cP. Examples of HPMCs having high viscosity include Methocel™ E10M, Methocel™ K15M and Methocel™ K100M, 2% by weight aqueous solutions of which have viscosities of 10,000 cP, 15,000 cP and 100,000 cP respectively. Various HPMC products are described in Anon. (1997) *Formulating for Controlled Release with Methocel Premium Cellulose Ethers*, Dow Chemical Co. The methoxyl and hydroxypropoxyl substitution type and content for selected HPMC products is provided in Table 1, below.

TABLE 1

| Properties of selected HPMC products | | |
|---|---|---|
| Methocel ™ E4MP (USP 2910) | Nominal Viscosity, 2% in Water | 4,000 cP |
| | Methoxyl, % | 28–30 |
| | Hydroxypropoxyl, % | 7–12 |
| Methocel ™ K4MP (USP 2208) | Nominal Viscosity, 2% in Water | 4,000 cP |
| | Methoxyl, % | 19–24 |
| | Hydroxypropoxyl, % | 7–12 |
| Methocel ™ E10MP | Nominal Viscosity, 2% in Water | 10,000 cP |

TABLE 1-continued

| Properties of selected HPMC products | | |
|---|---|---|
| (USP 2910) | Methoxyl, % | 28–30 |
| | Hydroxypropoxyl, % | 7–12 |
| Methocel ™ K15MP (USP 2208) | Nominal Viscosity, 2% in Water | 15,000 cP |
| | Methoxyl, % | 19–24 |
| | Hydroxypropoxyl, % | 7–12 |

An illustrative presently preferred HPMC with sustaining properties is one with substitution type 2208, denoting about 19% to about 24% methoxyl substitution and about 7% to about 12% hydroxypropoxyl substitution, and with a nominal viscosity, 2% in water, of about 4000 cP. A "controlled release" grade is especially preferred, having a particle size such that at least 90% passes through a 100-mesh screen. An example of a commercially-available HPMC meeting these specifications is Methocel™ K4M of Dow Chemical Co.

Without being bound by any particular hypothesis as to how the HPMC matrix according to the invention provides superior sustained-release characteristics, it is believed that upon oral ingestion and contact with gastrointestinal fluids, HPMC on or close to the tablet surface partially hydrates and thereby swells to form a gel layer having the active ingredient, e.g., celecoxib, distributed in a three-dimensional matrix therein. It is further believed that this outer three-dimensional gel matrix layer slows dissolution of the tablet. As the outer gel layer slowly dissolves, disperses or erodes, celecoxib is released from this layer into the gastrointestinal fluid where it is available for absorption. Meanwhile, hydration of the HPMC matrix gradually advances towards the center of the tablet, permitting further release of celecoxib over time by the same process hypothetically described above. Since the active ingredient is distributed throughout the tablet at a more or less uniform concentration throughout the HPMC matrix, a fairly constant amount of active ingredient can, according to the present non-limiting theory, be released per unit time in vivo by dissolution, dispersion or erosion of the outer portions of the tablet.

Overall release rate and consequently drug availability are dependent on the rate of diffusion of the drug through the outer gel layer and the rate of erosion of this layer of the tablet. Preferably T-90% (the time required for 90% drug release) in vivo is less than 24 hours, so that a clearance time exists whereby the tablet is suitable for once-a-day administration.

Dual-release matrix tablets of the invention can be prepared for example by co-compressing a first granulated mixture containing a selective COX-2 inhibitory drug in nanoparticulate form with a second granulated mixture containing a selective COX-2 inhibitory drug in an HPMC matrix. The first granulated mixture can be prepared according to information provided hereinabove. The second granulated mixture can be prepared illustratively as follows.

A mixer (e.g., a 60 liter Baker Perkins blender) is loaded with lactose, micronized selective COX-2 inhibitory drug, microcrystalline cellulose (e.g., an Avicel™ product), HPMC (e.g., Methocel™ K4M), and a binder (e.g., Pharmacoat™ 603), preferably in this order. These materials are mixed, for example for three minutes with a slow main blade setting and a slow chopper blade setting, to form a dry powder mixture.

The dry powder mixture is wet granulated, conveniently in the same blender with the main blade and chopper blade on a fast speed setting. Water is added in an amount and at a rate appropriate to the amount of dry powder mixture, illustratively at about 1–1.5 kg/minute for about 3 minutes. The resulting wet granulated mixture is blended for an additional period of time to ensure uniform distribution of water in the granulation. The wet granulated mixture contains about 30% water by weight.

The wet granulated mixture is dried, for example in an Aeromatic fluid bed dryer with inlet air temperature set at about 60° C., to reduce the moisture content to about 1% to about 3% by weight. Moisture content of the granules can be monitored, for example using a Computrac Moisture Analyzer.

The resulting dry granules are milled and screened, for example by passing through a Fitzpatrick mill (D6A) with 20-mesh screen, knives forward and medium speed setting (1500–2500 rpm).

The resulting screened granules are placed in a mixer, for example a Paterson-Kelley 2 cubic foot V-blender. Talc is added to the granules and the granules are blended for about 5 minutes. Magnesium stearate is then added to the granules and the granules are blended for about 3 minutes. The resulting lubricated granules are ready for co-compression together with the first granulated mixture to form dual-release matrix tablets.

In another particularly preferred embodiment of the present invention, the second fraction of selective COX-2 inhibitory drug is present in a multiplicity of solid beads, pellets or granules each having a coating comprising a polymer, preferably a release-extending polymer. Such beads, pellets or granules are referred to herein as "beads" or "coated beads" and are typically dense, hard, substantially spherical and of low friability. Compositions of this embodiment of the invention are referred to for convenience herein as "dual-release coated bead compositions". When formulated as capsules, which are a preferred dosage form for this embodiment, such compositions are referred to herein as "dual-release coated bead capsules". In such dual-release coated bead capsules, there can be separate sustained-release and immediate-release beads, or each bead can contain both immediate-release and sustained-release fractions and thereby have dual-release properties. Such dual-release beads are described in greater detail below.

In a dual-release coated bead composition of the present invention, whether encapsulated or tableted, the first fraction of selective COX-2 inhibitory drug can be present in any suitable immediate-release form but is preferably in nanoparticulate form and is preferably formulated into beads of similar size to the coated beads containing the second, sustained-release, fraction of celecoxib. Such beads containing the first, immediate-release, fraction are either uncoated or coated with a material that does not slow or extend release of the celecoxib. The demands of a dual-release selective COX-2 inhibitory drug composition are met surprisingly well by a dual-release coated bead preparation wherein the beads containing the sustained-release fraction of selective COX-2 inhibitory drug are coated with a barrier layer comprising at least one release extending polymer. The beads optionally contain pharmaceutically acceptable excipients such as lactose and microcrystalline cellulose and are preferably about 0.1 mm to about 1.0 mm, more preferably about 0.15 mm to about 0.5 mm, in diameter. For example, the beads can be of such a range of sizes that they pass through a 0.425 mm sieve but are retained on a 0.18 mm sieve. The beads can be prepared by mixing and granulation of the selective COX-2 inhibitory drug with one or more excipients, followed by extrusion, spheronization, drying and sieving the particles to the desired size range, followed by application of a polymer, preferably a release-extending polymer coating to the beads containing that fraction of the selective COX-2 inhibitory drug that is desired to exhibit sustained release.

In another embodiment, the beads have a core comprising a pharmaceutically acceptable excipient such as starch or sucrose, surrounded by one or more shells each comprising an inner drug-containing layer and an outer polymer barrier layer, preferably a release-extending polymer barrier layer. Beads according to this embodiment are preferably about 0.5 mm to about 2 mm, more preferably about 0.5 mm to about 1 mm, in diameter.

In a sustained-release coating preferred according to the present invention, the beads containing the second fraction of selective COX-2 inhibitory drug together with one or more excipients are coated with one or more polymers selected from HPMC, hydroxypropylcellulose, hydroxyethylcellulose, methylhydroxyethylcellulose, methylcellulose, ethylcellulose (e.g., Surelease™ of Colorcon), cellulose acetate, sodium carboxymethylcellulose, polymers and copolymers of acrylic acid and methacrylic acid and esters thereof (e.g., Eudragit™ RL, Eudragit™ RS, Eudragit™ L100, Eudragit™ S 100, Eudragit™ NE), polyvinylpyrrolidone and polyethylene glycols. The polymers can be combined with water-soluble substances such as sugar, lactose and salts to form a coating providing a pH-independent or pH-dependent release rate.

Eudragit™ of Rohm Pharma is a trade name applied to a range of products useful for film coating of sustained-release particles. These products are of varying solubility in gastrointestinal fluids. Eudragit™ RL and Eudragit™ RS are copolymers synthesized from acrylic and methacrylic esters with a low content of quaternary ammonium groups. Eudragit™ RL and Eudragit™ RS differ in the mole ratios of such ammonium groups to the remaining neutral (meth) acrylic acid esters (1:20 and 1:40 respectively). Eudragit™ NE is an aqueous dispersion of a neutral copolymer based on ethyl acrylate and methyl methacrylate. Characteristics of Eudragit™ polymers are described in *Eudragit: Sustained-release Formulations for Oral Dosage Forms*, Rohm Basic Info 2.

Ethylcellulose, available as an aqueous dispersion, for example under the trade name Surelease™, is another suitable material which is available in different grades and in special qualities for preparing barrier coatings. According to the invention it is preferred to use ethylcellulose having a viscosity of about 5 cP to about 15 cP, but other types of cellulose-based polymers can be used. It is especially preferred to use ethylcellulose in combination with HPMC.

The coating procedure can be performed by conventional means employing, for example, spraying equipment, a fluidized bed and equipment for drying and size fractionating. The liquid used in the coating procedure contains one or more barrier layer forming components and one or more solvents, such as ethanol, acetone, methyl isobutyl ketone (MIBK), water and others well known in this technical field. The coating liquid can be in the form of a solution, a dispersion, an emulsion or a melt, depending on the specific nature of the coating constituents.

Plasticizers and pigments can optionally be used to modify the technical properties or change the permeability of the coating. The coating preferably has virtually pH independent permeability properties throughout a pH range of 1.0 to 7.0. At higher pH a reduction in the release rate of certain drugs such as celecoxib may be observed but this is not due to the properties of the polymeric layer but to reduced solubility of the drug at high pH values.

An illustrative suitable coating composition according to the invention comprises ethylcellulose and HPMC together with a plasticizer such as triethyl citrate or coconut oil. A specific example of such a coating composition contains 90% polymer consisting of ethylcellulose and HPMC in a weight ratio of 55:35 to 80:10, with 10% triethyl citrate.

Each coated bead containing a selective COX-2 inhibitory drug represents an individual controlled release unit, releasing the drug at a predetermined rate, preferably independent of its position in the gastrointestinal tract. Overall dissolution profile and drug availability are dependent on the rate of drug diffusion through the sustained-release coating and/or on the rate of erosion of the coating in the gastrointestinal tract.

In a process for preparing a coated bead composition, a selective COX-2 inhibitory drug and diluents, preferably lactose and/or microcrystalline cellulose, are mixed and granulated by the following illustrative method. The drug is added to a mixture of lactose and microcrystalline cellulose (e.g., Avicel™ PH-101, Avicel™ RC-581, Avicel™ RC-591 or a mixture thereof) in a total amount of 1000–4000 g and dry-mixed in a high shear mixer (e.g., Niro-Fielder mixer) at a high mixing speed for 2–5 minutes. Water (300–700 grams) is added and the resulting mass is granulated for 2–5 minutes at high speed.

Extrusion of the resulting material can be performed for example in a NICA E-140 extruder (Lejus Medical AB, Sweden) through a perforated screen with drilled orifices of 0.25–1.0 mm diameter. The speed of the agitator and the feeder are preferably set on the lowest values.

Spheronization of the resulting extrudate can be conducted for example in a NICA Marumerizer (Ferro Mecano AB, Sweden). The speed of the Marumerizer plate is preferably adjusted to 500–10,000 rpm. Spheronization continues for 2–10 minutes, with about 1000 g wet extrudate on the plate at each run.

Drying of the resulting spheronized beads can be performed in a fluidized bed dryer (e.g., Aeromatic AG, West Germany) at an inlet temperature of 50–90° C. A net device can be placed in the top of the fluidized bed to avoid loss of beads to the cyclone output. The batch is preferably divided into sub-batches of 200–800 g. Each sub-batch is dried for 10–60 minutes at an air volume of 100–400 m$^3$/h in order to obtain individual beads rather than aggregates. If necessary, the sub-batches are then mixed and the whole batch dried for 5–30 minutes to an end product temperature of 40–60° C. A yield of dry beads of 1600–2000 g can be expected.

Sizing of the resulting dry beads can be performed using analytical sieves. Two sieves are selected from a set of sieve sizes, for example of 850 μm, 600 μm, 425 μm, 300 μm, 250 μm and 180 μm.

Selective COX-2 inhibitory drug beads manufactured as above can be coated with polymers, preferably release-extending polymers to prepare sustained-release coated beads. Immediate-release beads are not so coated. Both sustained-release and immediate-release beads are present in a dual-release composition of the invention. For example, Surelease™ or Eudragit™ RS can be applied as a 10–20% by weight solids dispersion, using spray coating equipment (e.g., Wurster). The spray gun is mounted at a height of 0.25 cm to 5 cm over the bottom of the bed. Beads prepared as above are preferably pre-heated. The coating is applied using the following typical process parameters: atomizing pressure 1.0–3.0 bar, air temperature 50–80° C., air velocity 100–400 m$^3$/h and solution flow about 10–80 ml/minute.

The coated beads manufactured as above, together with immediate-release beads, are encapsulated by a conventional encapsulation process.

In an illustrative process for preparing a composition of the invention having dual-release beads, the first fraction of drug is dispersed in a liquid medium in which the drug is substantially insoluble, preferably an aqueous medium, to form a first drug suspension, which is then wet milled. Milling conditions can be readily optimized by one skilled in the art to provide drug particles of a desired size range. The wet milled drug suspension is then spray coated onto sugar spheres. Next, a liquid polymer coating comprising one or more release-extending polymers and water is prepared. The polymer coating is then sprayed on top of the drug-coated sugar beads using any suitable spraying apparatus to form sustained-release beads.

Next, a second drug suspension comprising the second fraction of the drug is prepared in similar fashion to the first drug suspension. Additionally, a disintegrant suspension, for example comprising a disintegrant (e.g., croscarmellose sodium) and water, is prepared and wet milled. The second drug suspension and the milled disintegrant suspension are then mixed together to form a drug/disintegrant suspension. The drug/disintegrant suspension is then sprayed on top of the sustained-release beads prepared as above using any suitable spray coating equipment. All spray coating conditions can be readily optimized by one skilled in the art to provide a desired rate of coating and coat thickness.

The dual-release beads manufactured as above are encapsulated by a conventional encapsulation process.

EXAMPLES

Example 1

Preparation of Immediate-Release Celecoxib Spray Dried Powder

1. An aqueous drug suspension comprising 13.8% celecoxib, 2.8% povidone K30, 0.1% sodium lauryl sulfate and 83.3% deionized water was prepared.

2. The drug suspension was wet milled using a Wily A Bachofen DynoMill model KDL wet mill under the following conditions: (a) grinding chamber: 0.15 liter, batch mode; (b) grinding media: 0.7–1.0 mm lead-free glass beads; (c) grinding media volume: 125 ml (bulk volume); (d) agitation speed: 3000 rpm; (e) duration: 60 minutes. The median volume particle size of the milled suspension was determined by light diffraction to be 0.8 μm.

3. Lactose anhydrous (11% by weight) was dissolved in the milled drug suspension.

4. The milled suspension was then spray dried in a Yamato GB-21 spray drier under the following conditions: (a) powder-collection: cyclone; (b) inlet temperature: 110–130° C.; (c) outlet temperature: 60–70° C.; (d) spray rate: 3–5 ml/min; (e) airflow: 30–50% full-scale; (f) atomization pressure: 1 bar.

Final theoretical composition of the spray dried powder (% of total) was as follows: 48.3% celecoxib, 41.5% lactose, 9.7% povidone and 0.5% sodium lauryl sulfate.

Example 2

Preparation of Sustained Release Celecoxib Film-Coated Beads

1. An aqueous drug suspension comprising 30% celecoxib, 1.1% povidone K30 and 68.9% deionized water was prepared.
2. The drug suspension was wet milled using a Wily A Bachofen DynoMill model KDL wet mill under the following conditions: (a) grinding chamber: 0.3 liter, batch mode; (b) grinding media: 0.7–1.0 mm lead-free glass beads; (c) grinding media volume: 240 ml (bulk volume); (d) agitation speed: 3000 rpm; (e) flow rate: 40 ml/min.
3. An aqueous dispersion comprising Surelease™ E-7-19010 Clear (Colorcon) (41.2%), HPMC 2910 USP (4.5%) and deionized water (53.5%) was prepared.
4. The drug suspension was spray coated onto sugar spheres (25 g of 20–25 mesh sugar spheres NF) using a custom built, tangential spray 3.5 inch rotary processor as under the following conditions: (a) nozzle: Paasche VLS, size 5 nozzle tip; (b) atomization pressure: 17 psi; (c) rotary speed: 300 rpm; (d) drying air volume: 3 cfm; (e) drying air temperature: 70° C.; (f) spray rate: 0.2–0.4 g/min.
5. The polymer coating was then applied on top of the drug suspension coating using the same fluidized bed coater, configuration, and process conditions as in Step 4. A theoretical coating level of 6% (based on final coated bead weight) was applied. Final compositions of film-coated beads, based on a 95% coating efficiency, were as follows (% of total): 52.5% sugar sphere; 40.0% celecoxib; 1.5% povidone; 4.0% Surelease™ solids; 1.5% HPMC.

Example 3

Preparation of Celecoxib Dual-Release Beads

1. An aqueous disintegrant suspension comprising 5.0% croscarmellose sodium NF and 95% deionized water was prepared.
2. The disintegrant suspension was wet milled in a McCrone micronizing mill (Model 232) under the following conditions: (a) grinding chamber: polyethylene, McCrone model 232J with 232P cap; (b) grinding media: 48 agate cylinders, model 232A; (c) amount milled: 3 g croscarmellose sodium, 20 ml water; (d) amount of water for rinsing: 57 ml (mixed with milled suspension); (e) grinding duration: 10 minutes.
3. An aqueous drug suspension comprising 30% celecoxib, 1.1% povidone K30 and 68.9% deionized water was prepared and milled according to the same procedure described in Example 2.
4. The disintegrant suspension prepared in step 2 was mixed with the drug suspension prepared in step 3 to form a drug/disintegrant suspension. The composition of the drug/disintegrant suspension, by weight, was as follows: 22.6% celecoxib, 0.9% povidone, 1.3% croscarmellose sodium and 75.2% deionized water.
5. The drug/disintegrant suspension was spray coated onto film-coated beads (prepared as in Example 2) using a custom built, tangential spray 3.5 inch rotary processor under the following conditions: (a) nozzle: Paasche VLS, size 5 nozzle tip, (b) atomization pressure: 17 psi; (c) rotary speed: 300 rpm; (d) drying air volume: 3 cfm; (e) drying air temperature: 70° C.; (f) spray rate: 0.2–0.4 g/min.

Final composition of dual-release beads, assuming 90% to 95% coating efficiency, were as follows (% of total): 40.8% sugar sphere; 31.3% celecoxib (sustained-release layer); 1.1% povidone; 3.1% Surelease™ solids; 1.3% HPMC; 20.5% celecoxib (immediate-release layer); 0.8% povidone (immediate-release layer); 1.1% croscarmellose sodium (immediate-release layer).

Example 4

Four different prototype hard gelatin capsule formulations (dual-release Capsules A and B, sustained-release Capsule C and immediate-release Capsule D) were prepared containing beads and/or powder produced in Examples 1–3, above. All capsules were prepared using opaque white Capsugel™ size #0 ConiSnap™ hard gelatin capsules.

Formulation designs are shown in Table 2, below. Capsules A and B each contained both an immediate-release component and a sustained-release component. Capsule C contained only a sustained-release component while Capsule D contained only an immediate-release component.

TABLE 2

Formulation design of Capsules A–D

| Capsule Formulation | Immediate Release Component | Sustained Release Component | Dual Release Component |
|---|---|---|---|
| A | Spray dried powder (160 mg) | Film-coated beads (300 mg) | — |
| B | — | — | Dual-release beads (400 mg) |
| C | — | Film-coated beads (500 mg) | — |
| D | Spray dried powder (400 mg) | — | — |

As is shown in Table 2, Capsule A contained 160 mg of immediate-release spray dried powder (containing approximately 80 mg celecoxib) prepared as described in Example 1 and 300 mg of sustained release film-coated beads (containing approximately 120 mg celecoxib) prepared as described in Example 2. Capsule B contained 400 mg of dual-release beads prepared as described in Example 3. Capsule C contained 500 mg of film-coated beads prepared as described in Example 2. Capsule D contained 400 mg of spray dried powder prepared as described in Example 1. Total celecoxib loading of each of the four capsule formulations was approximately 200 mg.

Example 5

Capsules A-D and a commercial celecoxib 200 mg (immediate-release) capsule were tested in a standard USP dissolution assay performed using a Hanson model SIP autosampler under the following conditions: (a) dissolution medium was 1 liter of 0.05M sodium phosphate with 1% sodium lauryl sulfate; (b) paddles were rotated at 50 rpm; (c) 1 capsule was loaded per flask using copper wire capsule sinkers (3–5 twists); (d) 45 μm manual filtration was used from 0–1 h and Hanson autosampling was used from 2–24 h; and (e) HPLC with UV detection was used to analyze filtrate.

Results of the dissolution assay, shown in FIG. 1, demonstrate that dual release of celecoxib is achieved from both Capsule A comprising spray dried powder and film-coated beads, and from Capsule B comprising dual-release beads. It should be noted that the dissolution medium was selected to provide dissolution in under 30 minutes, not necessarily to reflect dissolution in vivo.

What is claimed is:

1. A pharmaceutical composition comprising one or more orally deliverable dose units, each comprising a first fraction of celecoxib in an amount of about 10 mg to about 400 mg, said first fraction being in solution in a pharmaceutically acceptable solvent and/or present in immediate-release solid particles having a $D_{90}$ particle size less than about 1 μm; and a second fraction of the celecoxib in an amount of about 10 mg to about 400 mg, said second fraction being present in solid particles having a $D_{90}$ particle size greater than about 25 μm and/or in controlled-release, slow-release, programmed-release, timed-release, pulse-release, sustained-release or extended-release particles; wherein said first fraction and said second fraction of the celecoxib are present in a weight ratio of about 10:1 to about 1:10.

2. The composition of claim 1 wherein said first fraction of the celecoxib is in solution in a pharmaceutically acceptable solvent.

3. The composition of claim 2 wherein the solvent comprises polyethylene glycol.

4. The composition of claim 2 wherein particles comprising said second fraction of the celecoxib are in stable suspension in a matrix solution comprising said first fraction of the celecoxib.

5. The composition of claim 4 that is in the form of unit dose soft capsules.

6. The composition of claim 1 wherein said first fraction of the celecoxib is present in immediate-release solid particles having a $D_{50}$ particle size less than about 5 μm.

7. The composition of claim 6 that is in the form of unit dose hard capsules.

8. The composition of claim 7 wherein said first fraction and said second fraction of the celecoxib are present in separate granules or beads within the capsules.

9. The composition of claim 8 wherein said second fraction of the celecoxib is present in a multiplicity of coated beads having controlled-release, slow-release, programmed-release, timed-release, pulse-release, sustained-release or extended-release properties.

10. The composition of claim 9 wherein the beads each have a sustained-release coating that comprises one or more pharmaceutically acceptable release-extending polymers.

11. The composition of claim 10 wherein said first fraction of the celecoxib is present in a multiplicity of beads similar in size to the beads containing said second fraction of the celecoxib, but having no coating or having a coating that is not a controlled-release, slow-release, programmed-release, timed-release, pulse-release, sustained-release or extended-release coating.

12. The composition of claim 10 wherein the release-extending polymers are selected from ethylcellulose and polymers and copolymers of acrylic acid, methacrylic acid and esters thereof.

13. The composition of claim 7 wherein said first fraction and said second fraction of the celecoxib are present together in beads, each individual bead having dual-release properties.

14. The composition of claim 13 wherein each bead has an inner sustained-release layer containing said second fraction of the celecoxib and an outer immediate-release layer containing said first fraction of the celecoxib.

15. The composition of claim 6 that is in the form of unit dose tablets.

16. The composition of claim 15 wherein said first fraction and said second fraction of the celecoxib are present in separate layers within the tablets.

17. The composition of claim 16 wherein said second fraction of the celecoxib is present in particles having controlled-release, slow-release, programmed-release, timed-release, pulse-release, sustained-release or extended-release properties.

18. The composition of claim 17 wherein said second fraction of the celecoxib is distributed in a sustained-release matrix comprising hydroxypropylmethylcellulose having a viscosity, 2% in water, of about 100 to about 8000 cP.

* * * * *

UNITED STATES PATENT AND TRADEMARK OFFICE
CERTIFICATE OF CORRECTION

PATENT NO. : 7,220,434 B2  Page 1 of 1
APPLICATION NO. : 10/169039
DATED : May 22, 2007
INVENTOR(S) : Desai et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by 2 days Delete the phrase "by 2 days" and insert -- by 0 days --

Signed and Sealed this

Fourth Day of November, 2008

JON W. DUDAS
*Director of the United States Patent and Trademark Office*